United States Patent
Yokosawa et al.

[11] Patent Number: 5,829,439
[45] Date of Patent: Nov. 3, 1998

[54] NEEDLE-LIKE ULTRASONIC PROBE FOR ULTRASONIC DIAGNOSIS APPARATUS, METHOD OF PRODUCING SAME, AND ULTRASONIC DIAGNOSIS APPARATUS USING SAME

[75] Inventors: Koichi Yokosawa, Kokubunji; Shizuo Ishikawa, Kanagawa-ken; Ryuichi Shinomura, Higashimatsuyama; Yukio Ito, Machida; Shuzo Sano, Kashiwa; Hiroshi Kanda, Tokorozawa; Yutaka Sato, Kashiwa; Toshio Kondo, Kunitachi, all of Japan

[73] Assignee: Hitachi Medical Corporation, Tokyo, Japan

[21] Appl. No.: 671,010

[22] Filed: Jun. 28, 1996

[30] Foreign Application Priority Data

Jun. 28, 1995 [JP] Japan .................................. 7-161960
Oct. 16, 1995 [JP] Japan .................................. 7-291697

[51] Int. Cl.⁶ .................................................. A61B 8/00
[52] U.S. Cl. ................................ 128/662.06; 128/662.05
[58] Field of Search ..................... 128/662.06, 662.05, 128/662.03, 663.01, 660.08, 660.09, 660.1

[56] References Cited

U.S. PATENT DOCUMENTS 4,911,172  3/1990  Bui et al. ............................ 128/662.05
5,167,234  12/1992 Watanabe et al. .................. 128/662.06
5,199,437  4/1993  Langberg ............................ 128/662.06
5,209,721  5/1993  Wilk .................................... 128/662.05
5,402,792  4/1995  Kimura ............................... 128/663.01

FOREIGN PATENT DOCUMENTS 4-78299  12/1992  Japan .
5-9097   2/1993   Japan .
6-125    1/1994   Japan .

Primary Examiner—George Manuel
Attorney, Agent, or Firm—Antonelli, Terry, Stout & Kraus, LLP.

[57] ABSTRACT

A needle-like ultrasonic probe includes an inner needle received in a hollow, tubular outer needle for rotation about an axis thereof. The inner needle has a pointed distal end, and a notch is formed in an outer peripheral surface of that portion of the inner needle which is located adjacent to the distal end thereof. At least one ultrasonic transducer, as well as an acoustic lens for converging an ultrasonic wave, produced by the ultrasonic transducer, onto a point near to the outer peripheral surface of the inner needle, is provided in the notch. A filler, having an outer surface conforming to the outer peripheral surface of the inner needle, is fitted in the notch. With this construction, after the inner needle is smoothly stuck into a living tissue, even if it is rotated and axially moved, the living tissue is less affected or damaged by the inner needle.

13 Claims, 14 Drawing Sheets

5,829,439

NEEDLE-LIKE ULTRASONIC PROBE FOR ULTRASONIC DIAGNOSIS APPARATUS, METHOD OF PRODUCING SAME, AND ULTRASONIC DIAGNOSIS APPARATUS USING SAME

BACKGROUND OF THE INVENTION

This invention relates to a needle-like ultrasonic probe which is designed to be stuck directly into a patient's body to be examined (hereinafter simply referred to as "patient's body") so as to obtain a high-resolution image of a localized part of the patient's body through ultrasonic waves, and the invention also relates to a diagnosis apparatus using such a needle-like ultrasonic probe.

RELATED ART

There are already known ultrasonic diagnosis apparatuses in which an ultrasonic probe is pressed against a surface of a patient's body adjacent to an affected part, or is inserted into a body cavity, and a tomographic image of the body is obtained, thereby making a diagnosis. With such ultrasonic diagnosis apparatuses, although the position of the affected part of the patient's body can be determined, it is difficult to accurately grasp the condition of a localized portion of the affected part.

Japanese Patent Examined Publication No. 5-9097 discloses an ultrasonic diagnosis apparatus in which a needle-like ultrasonic probe is stuck directly into the affected part of the patient's body determined by the above-mentioned tomographic image, and a high-resolution image in a localized portion of the affected part is obtained, thereby offering more accurate diagnosis. This needle-like ultrasonic probe comprises an outer needle of a hollow construction having an outer diameter of about 1 mm, an inner needle angularly movably mounted within the outer needle, and a transducer mounted on the inner needle for transmitting and receiving ultrasonic waves. This outer needle is first stuck into the affected part of the patient body, and then an ultrasonic signal is applied from the transducer to the affected part through an opening, formed through the outer needle, while angularly moving the inner needle, and the ultrasonic signal, reflected from the affected part, is received by the transducer, thereby obtaining ultrasonic photograph images of the affected part around the outer needle.

This needle-like ultrasonic probe will be described with reference to FIGS. 27, 28A and 28B.

FIG. 27 is a cross-sectional view of the above needle-like ultrasonic probe, and the inner needle 2, having a conical distal end, is provided within the outer needle 1 for reciprocal movement in the axial direction and for rotation (angular movement) about the axis, the outer needle 1 being made of a rigid material. A notch 4 is formed in an outer peripheral surface of the inner needle 2, and the ultrasonic transducer 3 is provided in this notch 4. The transducer 3 comprises an acoustic lens material 5 (serving as a base) made of sapphire, silicon or the like, and a lower electrode 7, a piezoelectric element 8 and an upper electrode 9 are provided on one surface 6 of the acoustic lens material 5, and a lens surface 11 of a concavely-spherical shape is formed in the other surface 10 of the acoustic lens material 5. When the lower electrode 7, the piezoelectric element 8 and the upper electrode 9 are energized, an ultrasonic wave 12 is produced, and this ultrasonic wave 12 is refracted and deflected by the lens surface 11, and the thus refracted ultrasonic wave 12' converges into a focus 13. Reference numeral 14 denotes an imaging area which the focus 13 covers when the inner needle 2 is rotated or angularly moved as in a direction of arrow B in FIG. 2, and reference numeral 15 denotes the patient body.

In this conventional needle-like ultrasonic probe, however, the other surface 10 of the acoustic lens material 5 adapted to make contact with the patient body is flat or concave while the inner needle 2 has, for example, a circular cross-section. Therefore, when effecting the ultrasonic scanning by rotating the inner needle 2, the tissue of the patient body 15 have been often caught and damaged by the flat or the concave portion. Since the other surface 10 of the acoustic lens material 5 is thus flat or concave, the degree of absorption of the ultrasonic wave 12' by the patient's body 15 in a path thereof from the focus 13 increases, so that the sound field has often been disturbed. Therefore, the picture quality of the obtained ultrasonic image has often been degraded.

In this conventional needle-like ultrasonic probe, only one ultrasonic transducer 3 is provided at the outer peripheral surface of the inner needle 2 in the vicinity of the distal end thereof, and therefore the stationary position of the focus 13 is fixed to one point, and the ultrasonic information, obtained in the direction of the depth for each piercing of the probe into the patient's body 15, is limited to only one kind. Therefore, for obtaining a plurality of kinds of ultrasonic informations from the affected part of the patient's body 15, it has been necessary to repeatedly pierce the needle-like ultrasonic probe into the patient's body 15, which has increased the burden on the patient. And besides, with the only one ultrasonic transducer 3, only one fixed center frequency is used, and therefore the resolution of the obtained ultrasonic image is limited. Therefore, when it has been desired to observe the affected part of the patient's body 15 with higher precision, the ultrasonic transducer 3 must be exchanged by one having a higher center frequency, and the measurement must be effected several times by repeating this procedure. In this case, the needle-like ultrasonic probe must be repeatedly stuck into the patient's body as in the above case, and this has increased the burden on the patient.

Furthermore, with the use of the only one ultrasonic transducer 3, for scanning the affected part in a two-dimensional manner through the ultrasonic wave while rotating and translating (linearly moving) the inner needle 2, the inner needle 2 is rotated at a certain position to move the focus 13 at an imaging region 14 as shown in FIGS. 28A and 28B, and then the inner needle 2 is translated to another position, and then is again rotated there. Thus, this procedure must be repeated. Therefore, much time has been required for obtaining the ultrasonic images by scanning the entire imaging area 14 having an area, for example, of (a×b) as shown in FIG. 28B. This also increases the burden on the patient.

Such needle-like ultrasonic probes are also disclosed in Japanese Patent Examined Publication Nos. 4-078299 and 6-000125. More specifically, Japanese Patent Examined Publication No. 4-078299 discloses the needle-like ultrasonic probe in which a recess is formed in a needle, and an ultrasonic transducer is provided on a wall surface of this recess. Japanese Patent Examined Publication No. 6-000125 discloses the needle-like ultrasonic probe in which an inner needle and an ultrasonic transducer can be exchanged.

SUMMARY OF THE INVENTION

With the above problems of the prior art in view, it is a first object of this invention to provide a needle-like ultrasonic probe which can suppress the influence on the body's tissue as much as possible, and can obtain an ultrasonic image of a localized part of the body's tissue in a short period of time, and can obtain ultrasonic images of different measurement conditions at the same time by sticking the probe once into the body.

A second object of the invention is to provide a method of producing such a needle-like ultrasonic probe.

A third object of the invention is to provide a system in which a diagnosis can be easily carried out, using ultrasonic images obtained by energizing the above-mentioned needle-like ultrasonic probe.

According to one aspect of the present invention, there is provided a needle-like ultrasonic probe comprising:

a hollow, tubular outer needle which is made of a rigid material, and has a small diameter;

an inner needle which is made of a rigid material, and is in the form of a bar of a circular cross-section having a small diameter, the inner needle being received in the outer needle for rotation about an axis thereof and for translation along the axis thereof, and the inner needle having a distal end of a conical shape; and at least one ultrasonic transducer for transmitting and receiving an ultrasonic wave, said ultrasonic transducer being mounted at that portion of an outer peripheral surface of said inner needle disposed adjacent to said distal end thereof;

wherein said inner needle and said outer needle are stuck into a patient's body, and an ultrasonic wave is transmitted from and received by said ultrasonic transducer, and said inner needle is rotated and translated to effect two-dimensional scanning so as to obtain an ultrasonic image of a tissue of the patient's body; and wherein the outer peripheral surface of that portion of said inner needle, which is disposed adjacent to said distal end thereof, and has said ultrasonic transducer provided therein, is formed into an arc-shaped cross-section conforming to the cross-section of the outer peripheral surface of the other portion of said inner needle, and the entire outer peripheral surface of said inner needle is finished into a smooth surface.

A plurality of ultrasonic transducers mentioned above can be mounted on a common base which is mounted at that portion of the outer peripheral surface of said inner needle disposed adjacent to said distal end thereof, and which is composed of an acoustic lens material.

According to another aspect of the invention, there is provided a needle-like ultrasonic probe for being stuck into a living body so as to measure a living tissue therearound by an ultrasonic wave, said probe comprising:

an acoustic lens for converging the ultrasonic wave;

at least one ultrasonic transducer for transmitting and receiving the ultrasonic wave in a direction substantially perpendicular to an axis of said probe;

a sound-propagating medium interposed between said acoustic lens and the body's tissue to be measured; and means for causing the position of a focus, into which the ultrasonic wave, transmitted from and received by said ultrasonic transducer, is converged in said sound-propagating medium by said acoustic lens, to coincide with the position of an interface between said body's tissue and said sound-propagating medium (or a point of the body's tissue distant slightly from this interface) in the range of the depth of the focus of said acoustic lens at least during the measurement.

According to a further aspect of the invention, there is provided a needle-like ultrasonic probe for being stuck into a living body so as to measure a living tissue therearound by an ultrasonic wave, said probe comprising:

an acoustic lens for converging the ultrasonic wave;

at least one ultrasonic transducer for transmitting and receiving the ultrasonic wave in a direction substantially perpendicular to an axis of said probe; and conduit means for supplying and discharging a liquid sound-propagating medium:

wherein said liquid sound-propagating medium is supplied between said acoustic lens and the living tissue to be measured through said supply-discharge conduit means, thereby forming an image of the living tissue; and wherein said ultrasonic transducer is arranged on a spiral line around the axis of the probe.

According to a further aspect of the invention, there is provided a method of producing a needle-like ultrasonic probe comprising the steps of:

a plurality of lens surfaces are formed in one surface of an acoustic lens material by a mechanical process or a chemical process;

subsequently forming a lower electrode, piezoelectric elements and upper electrodes on the other surface of said acoustic lens material by vacuum deposition or sputtering in such a manner that said piezoelectric elements, as well as said upper electrodes, are located in registry with said plurality of lens surfaces, respectively;

subsequently cutting said acoustic lens material into a predetermined shape, thereby providing ultrasonic transducers;

subsequently mounting an intermediate base on said acoustic lens material, and connecting said intermediate base to said lower electrode and said upper electrodes by respective signal wires;

subsequently fixedly fitting said acoustic lens material in a mounting groove formed in that portion of an outer peripheral surface of an inner needle located adjacent to a distal end thereof;

subsequently connecting a cable to said intermediate base; and finally forming the outer peripheral surface of that portion of said inner needle, in which said acoustic lens material is fitted, into an arc-shaped cross-section conforming to the cross-section of the outer peripheral surface of the other portion of said inner needle, and finishing the entire outer peripheral surface of said inner needle into a smooth surface.

According to a further aspect of the invention, there is provided an ultrasonic diagnosis apparatus comprising:

a first probe for making contact with a surface of the patient's body;

means for driving said first probe so as to produce an ultrasonic tomographic image of a living tissue of the patient's body;

a needle-like ultrasonic probe for transmitting and receiving an ultrasonic wave; and means for sticking an inner needle of said needle-like ultrasonic probe and then for rotating and translating said inner needle so as to effect a two-dimensional scanning;

wherein while observing the tomographic image of an affected part through a monitor by operating said first probe, said inner needle is stuck into a required portion of the affected part by said drive means, and an image of the living tissue adjacent to a distal end portion of said inner needle is displayed on said monitor.

DESCRIPTION OF THE PREFERRED EMBODIMENTS

A preferred embodiment of the present invention will now be described with reference to the accompanying drawings.

Figure 1:
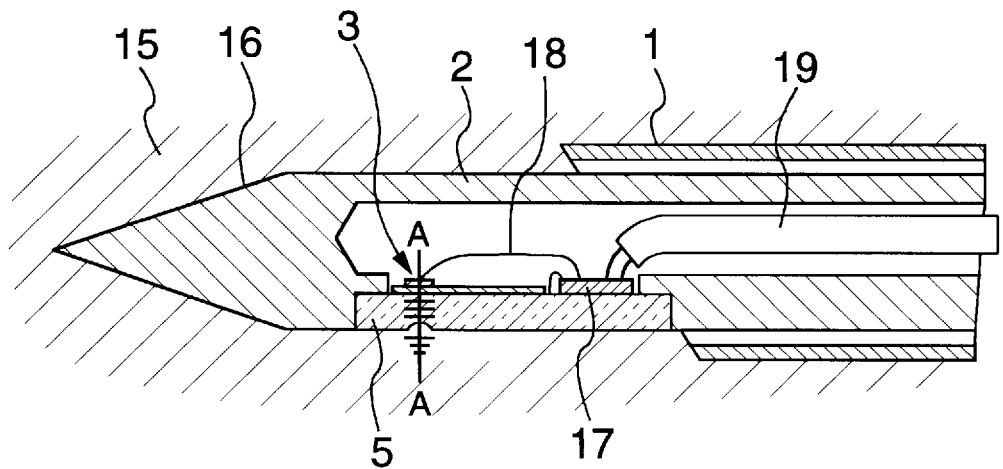
FIG. 1 is a longitudinal cross-sectional view illustrating a first embodiment of a needle-like ultrasonic probe of the invention, taken along a center axis thereof.

FIG. 1 is a longitudinal cross-sectional view of a first embodiment of a needle-like ultrasonic probe of the invention, taken along a center axis thereof. This needle-like ultrasonic probe is designed such that an ultrasonic transducer, provided at a distal end portion of a needle, is introduced directly into a living tissue of the patient's body, and an ultrasonic image of this living tissue is obtained by two-dimensional ultrasonic scanning. As shown in FIG. 1, the needle-like ultrasonic probe comprises an outer needle 1, an inner needle 2, and the ultrasonic transducer 3.

The outer needle 1 holds the inner needle 2 therein, and serves to guide the inner needle 2 when the inner needle 2 is stuck into the tissue of the patient's body 15. The outer needle 1 is made of a rigid material such as metal, and is in the form of a hollow pipe having a small outer diameter of about 2 mm. The inner needle 2 is inserted or received in the bore of the outer needle 1. The inner needle 2 holds the ultrasonic transducer 3 at an outer peripheral surface thereof, and can be stuck directly into the tissue of the patient's body 15. The inner needle 2 is made of a rigid material such as metal, and is in the form of a rod or bar of a circular cross-sectional shape having a small diameter of about 1 to 2 mm, and a distal end of the inner needle 2 is formed into a conical shape. The inner needle 2 is inserted in the outer needle 1 in coaxial relation thereto, with a small clearance defined therebetween, and the inner needle 2 is rotatable about an axis thereof as indicated by arrow B (FIG. 2), and also can be translated (linearly moved) along the axis thereof as indicated by arrow C.

Figure 2:
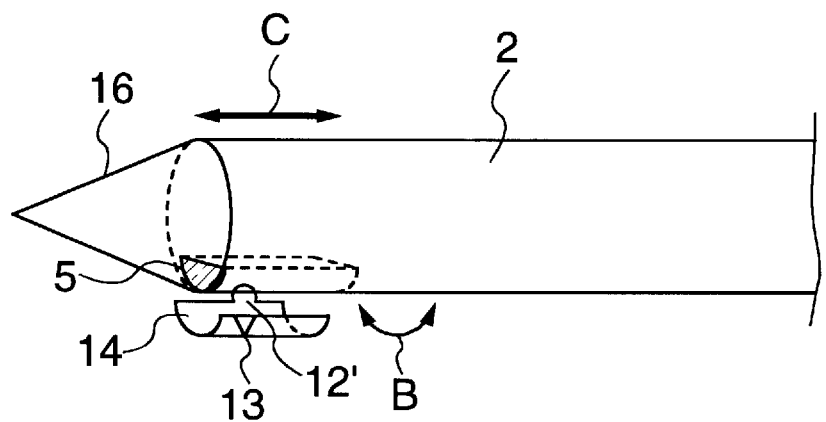
FIG. 2 is a perspective view showing the rotation and translation of an inner needle of the needle-like ultrasonic probe for two-dimensional scanning.
Figure 3:
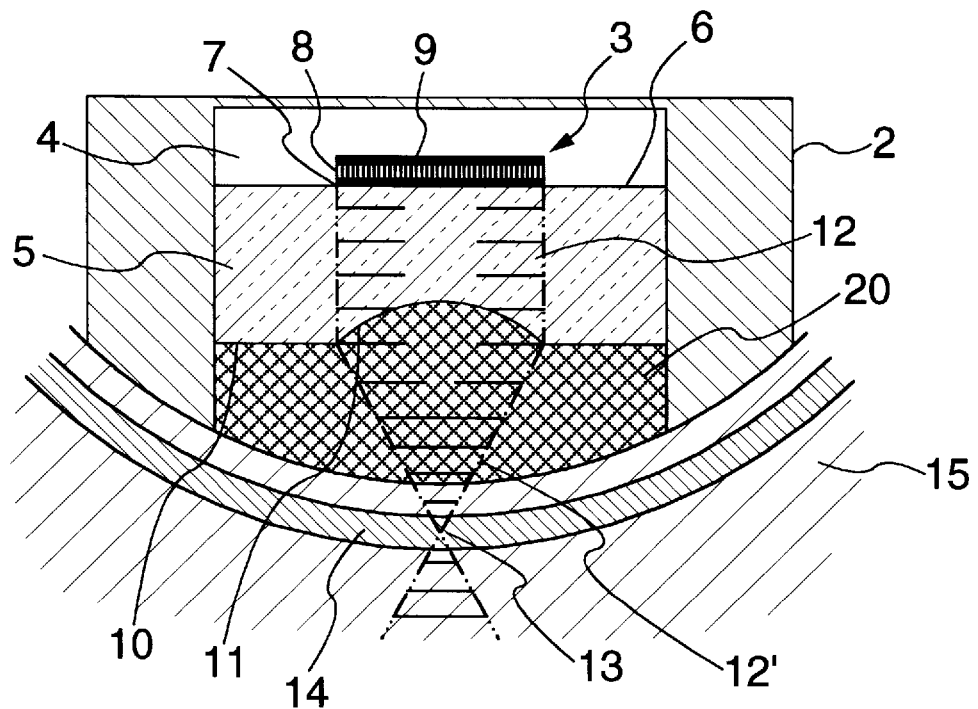
FIG. 3 is a enlarged, cross-sectional view taken along the line A—A of FIG. 1, showing the construction of an ultrasonic transducer.

The ultrasonic transducer 3 is mounted at that portion of the outer peripheral surface of the inner needle 2 located adjacent to the distal end 16 thereof. This ultrasonic transducer 3 transmits ultrasonic waves into the patient's body 15, and also receives an echo signal reflected from a living tissue. As shown in FIG. 3, a groove 4 is formed in a predetermined portion of the outer peripheral surface of the inner needle 2, and the ultrasonic transducer 3 is fitted and fixed in this groove 4. The ultrasonic transducer 3 comprises an acoustic lens material 5 (serving as a base) made of sapphire, silicon or the like, and a lower electrode 7, a piezoelectric element 8 and an upper electrode 9 are provided on one surface 6 of the acoustic lens material 5, and a lens surface 11 of a concavely-spherical shape is formed in the other surface 10 of the acoustic lens material 5. When the lower electrode 7, the piezoelectric element 8 and the upper electrode 9 are energized, an ultrasonic wave 12 is produced, and this ultrasonic wave 12 is refracted and deflected by the lens surface 11. Thus, the refracted ultrasonic wave 12' converges into a focus 13 which is located at a point of the body's tissue slightly distant from the interface between the acoustic lens material 5 and the body's tissue. Preferably, the focus 13 has a distance less than 1 mm from the interface, and more preferably it is in a range of 0.1 to 0.2 mm from the interface. Reference numeral 14 denotes an imaging area over which the focus 13 can cover when the inner needle 2 is rotated or angularly moved in the direction of arrow B in FIG. 2. As shown in FIG. 1, an intermediate base 17 is mounted on a part of the acoustic lens material 5, and the lower electrode 7 and the upper electrode 9 are connected or wire bonded to the intermediate base 17 by respective signal wires 18, and a cable 19 is connected at one end to the intermediate base 19, and is connected at the other end to a control device (not shown).

The inner needle 2 and the outer needle 1 are stuck into the patient's body 15, and the ultrasonic transducer 3 transmits an ultrasonic wave to the inside of the patient's body 15, and receives its reflection therefrom, and also the inner needle 2 is rotated in the direction of arrow B, and is translated in the direction of arrow C, thereby effecting the two-dimensional scanning, thus obtaining ultrasonic images of the tissue of the patient's body.

In the present invention, as shown in FIG. 3, the outer peripheral surface of that portion of the inner needle 2, which is located adjacent to the distal end thereof, and which holds the ultrasonic transducer 3 provided therein, is formed into an arc-shaped (or arcuate) cross-section conforming to the cross-section of the outer peripheral surface of the other portion of the inner needle 2, and the entire outer peripheral surface of the inner needle 2 is finished into a smooth surface. More specifically, a filler 20 is filled in a recess defined by the groove 4, and other surface 10 of the acoustic lens material 5 on which the lens surface 10 for the ultrasonic transducer 3 fitted in the groove 4 is formed, and the outer surface of this filler 20 is formed into an arc-shaped cross-sectional shape conforming to the cross-section of the outer peripheral surface of the other portion of the inner needle 2. The filler 20 is made of a material which is higher in acoustic velocity than the acoustic lens material (base) 5 of the ultrasonic transducer 3, and has a low acoustic impedance, low acoustic attenuation and good biological compatibility with the living body.

Thus, the inner needle 2 is finished so as to have, as a whole, the smooth outer peripheral surface as of a round rod, and accordingly, when the inner needle 2 is rotated in the direction of arrow B (FIG. 2) for effecting the ultrasonic scanning, it will not damage the tissue of the patient's body 15. As is clear from FIG. 3, since the arcuate outer surface of the filler 20 is located near to the focus 13 of the ultrasonic wave 12', the degree of absorption of the ultrasonic wave by the patient's body 15 is low, so that the sound field is prevented from being disturbed. Therefore, ultrasonic images of a high quality can be obtained. And besides, the focus 13 is located at a point of the living tissue slightly distant from the surface of contact (interface) between the filler 20 and the living tissue, and therefore, rather than the images of the body's tissue at the interface (which is liable to be damaged upon rotation of the inner needle 2), images of an undamaged living tissue can be obtained.

Figure 4:
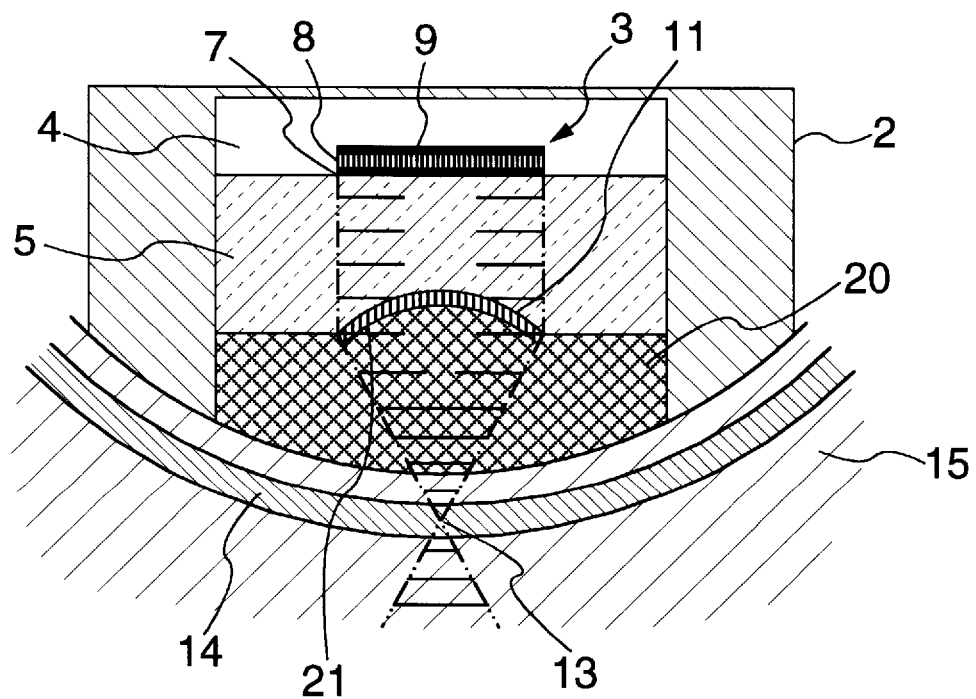
FIGS. 4 to 6 are views similar to FIG. 3, but showing modified forms of the one shown in FIG. 3, respectively.

FIG. 4 is a cross-sectional view of a modified form of the construction shown in FIG. 3. In this example, an acoustic matching layer 21 is formed on a concavely-spherical lens surface 11 of an ultrasonic transducer 3, and the above-mentioned filler 20 is filled outside thereof, and the outer surface of this filler 20 is formed into an arc-shaped cross-section conforming to the cross-section of the outer peripheral surface of the other portion of the inner needle 2. In this case, the ultrasonic sensitivity is higher than that obtained with the construction shown in FIG. 3, so that the picture quality can be further enhanced.

Figure 5:
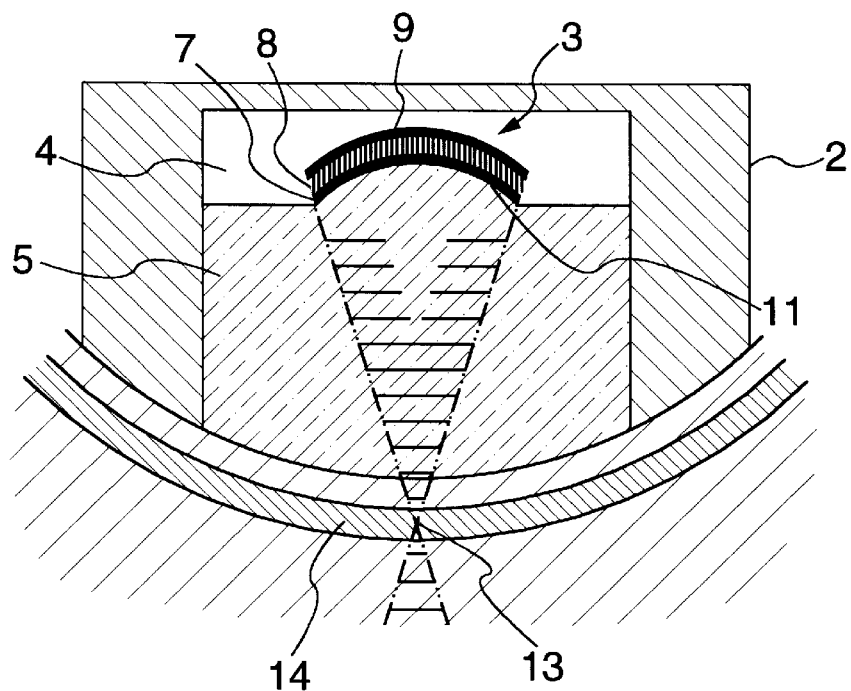

FIG. 5 is a cross-sectional view of another modified form of the construction shown in FIG. 3. In this example, a lens surface 11 of a convexly-spherical shape is formed on an inner surface of an acoustic lens material 5 of an ultrasonic transducer 3, and a lower electrode 7, a piezoelectric element 8 and an upper electrode 9 are laminated one upon another on the lens surface 11 in the mentioned order. An outer surface of the acoustic lens material 5 is formed into an arc-shaped cross-section conforming to the cross-section of the outer peripheral surface of the other portion of an inner needle 2, and the entire outer peripheral surface of the inner needle 2 is formed into a smooth surface. In this case, the provision of the filler 20 shown in FIG. 3 can be omitted.

Figure 6:
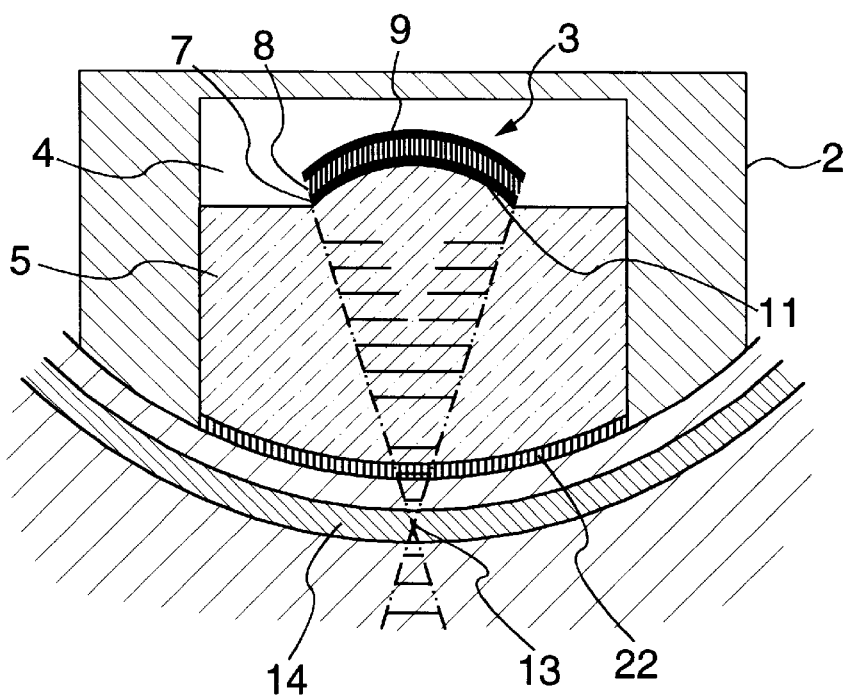

FIG. 6 is a cross-sectional view of a modified form of the construction of FIG. 5. In this example, an acoustic matching layer 22 is formed on an arcuate outer surface of an acoustic lens material 5, and an outer surface of this acoustic matching layer 22 is formed into an arc-shaped cross-section conforming to the cross-section of the outer peripheral surface of the other portion of an inner needle 2. In this case, the ultrasonic sensitivity is higher than that obtained with the construction of FIG. 5, so that the picture quality can be further enhanced.

Figure 7:
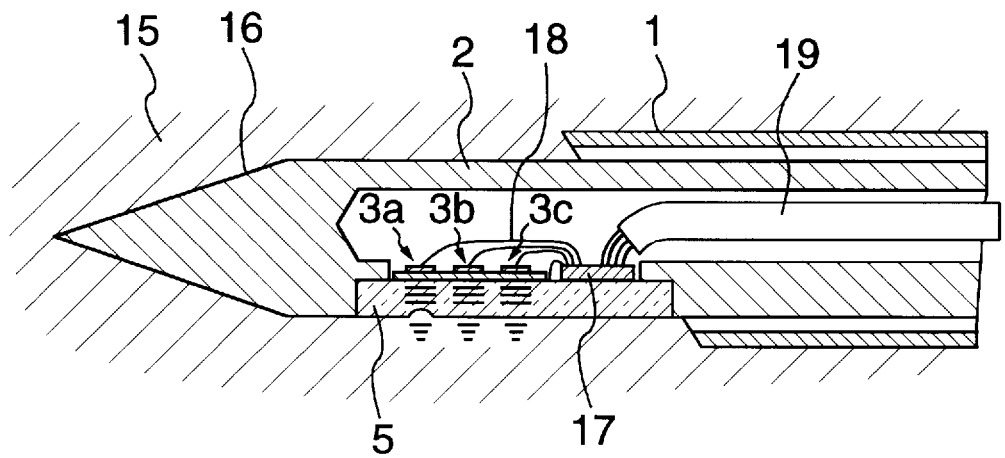
FIG. 7 is a longitudinal cross-sectional view illustrating a second embodiment of a needle-like ultrasonic probe of the invention, taken along an axis thereof.

FIG. 7 is a longitudinal cross-sectional view which shows a second embodiment of a needle-like ultrasonic probe of the invention, taken along an axis thereof. In this embodiment, a plurality of ultrasonic transducers 3a, 3b and 3c are provided on that portion of an inner needle 2 located adjacent to a distal end thereof, and these ultrasonic transducers 3a to 3c are mounted on an acoustic lens material (serving as a common base) 5 provided at an outer peripheral surface of the inner needle 2. More specifically, a lower electrode 7, a piezoelectric element 8 and upper electrodes 9 are stacked one upon another on one surface of the acoustic lens material (common base) 5 in the mentioned order, and lens surfaces 11 of a concavely-spherical shape are formed in the other surface of the acoustic lens material 5, thereby forming the ultrasonic transducers 3a, 3b and 3c which are juxtaposed and spaced at suitable intervals from one another along the axis of the inner needle 2. In this embodiment of FIG. 7, the common piezoelectric element 8 has a uniform thickness throughout its length and width, and the upper electrodes 9 have the same shape and the same diameter. The lens surfaces 11 have the same diameter. The plurality of ultrasonic transducers 3a, 3b and 3c have the same center frequency, and have the same upper electrodes 9, respectively, and have the same lens condition for converging a produced ultrasonic wave. This center frequency is high on the order of several tens of MHz to several hundreds of MHz, and a high resolution of several tens of $\mu$m can be obtained.

Figure 8A:
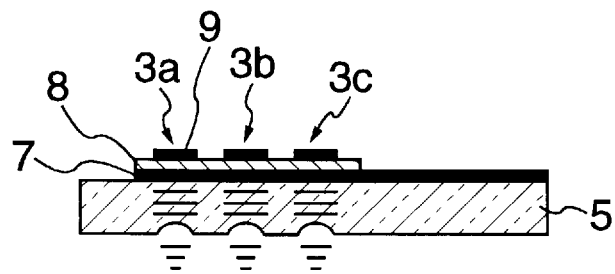
FIGS. 8A and 8B are views showing an imaging area covered by an ultrasonic scanning operation of the needle-like ultrasonic probe of FIG. 7.
Figure 8B:
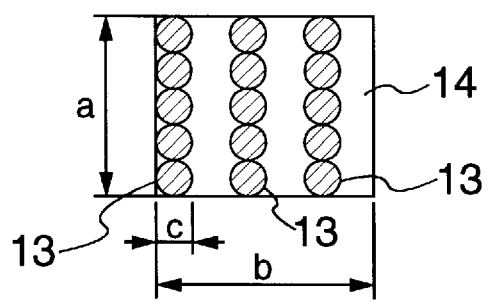
Figure 28A:
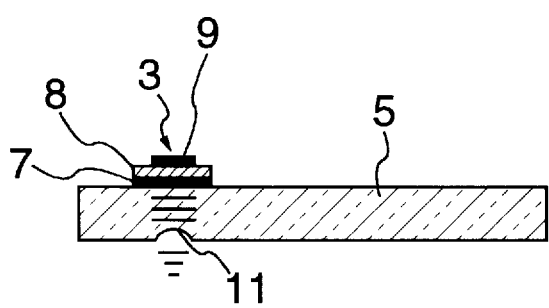
FIGS. 28A and 28B are views showing an imaging area over which ultrasonic scanning of the above conventional needle-like ultrasonic probe can cover.
Figure 28B:
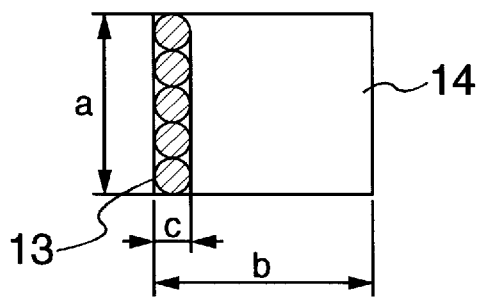

The plurality of ultrasonic transducers 3a, 3b and 3c are thus arranged in juxtaposed relation, and ultrasonic waves are scanningly applied from these transducers 3a, 3b and 3c in a two-dimensional manner by rotating the inner needle 2 as indicated by arrow B (FIG. 2) and translating the same as indicated by arrow C. At this time, when the inner needle 2 is rotated in the direction of arrow B in an imaging area 14 at a certain position to move or shift focuses 13, the three focuses 13 of the juxtaposed ultrasonic transducers 3a, 3b and 3c are moved for scanning, parallel to one another, as shown in FIGS. 8A and 8B. Therefore, when the two-dimensional scanning is made over the entire imaging area 14, having an area, for example, of (a×b), so as to obtain ultrasonic images as shown in FIG. 8B, the range, covered by one rotational scanning is three times as large as that obtained with the conventional construction of FIG. 28B, and therefore the time required for the scanning of the entire imaging area 14 can be reduced in this embodiment.

Figure 9:
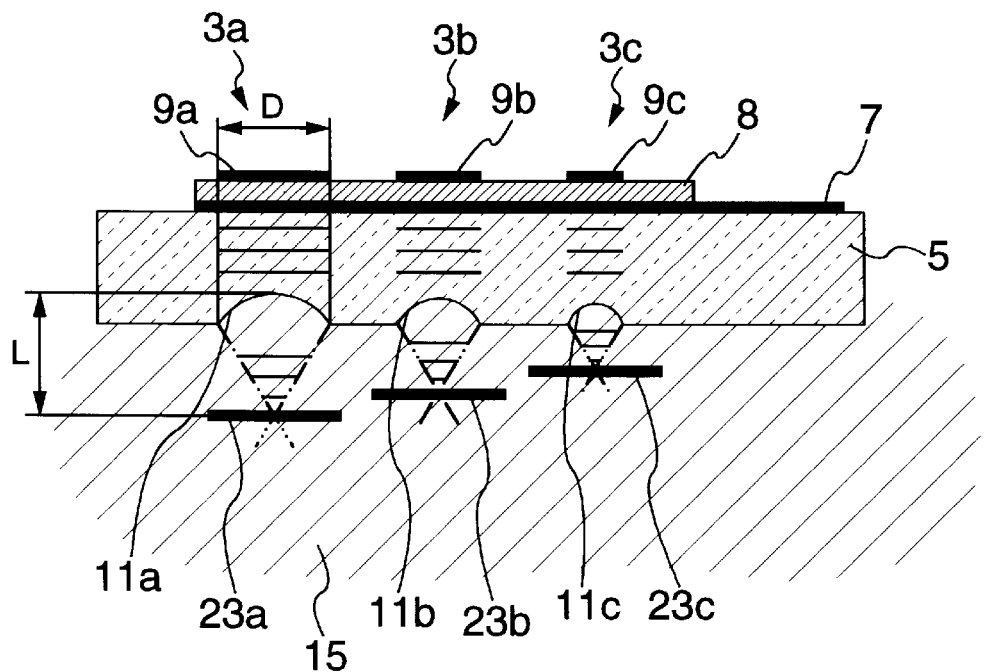
FIGS. 9 to 11 are longitudinal cross-sectional views illustrating modified forms of the embodiment shown FIG. 7, respectively, showing an ultrasonic transducer portion.

FIG. 9 is a longitudinal sectional view which shows a part, in which ultrasonic transducers are provided, of a modified form of the embodiment of FIG. 7, and more specifically is a longitudinal cross-sectional view showing an ultrasonic transducer portion. In this example, a common piezoelectric element 8 for a plurality of ultrasonic transducers 3a to 3c has a uniform thickness throughout its length and width, and upper electrodes 9a, 9b and 9c have different diameters D, respectively, and lens surfaces 11a, 11b and 11c have different diameters, respectively. The plurality of ultrasonic transducers 3a, 3b and 3c have the same center frequency, and have the different upper electrodes 9a, 9b and 9c, respectively, and different lens conditions, respectively, for converging produced ultrasonic waves. In this case, focal distances L of the ultrasonic transducers 3a, 3b and 3c are different from one another, and observation positions 23a, 23b and 23c of different depths in the patient's body 15 can be selected at the same time, and therefore without the need for repeating the sticking of the needle as in the conventional construction, ultrasonic images of the different observation positions 23a, 23b and 23c can be easily obtained.

Figure 10:
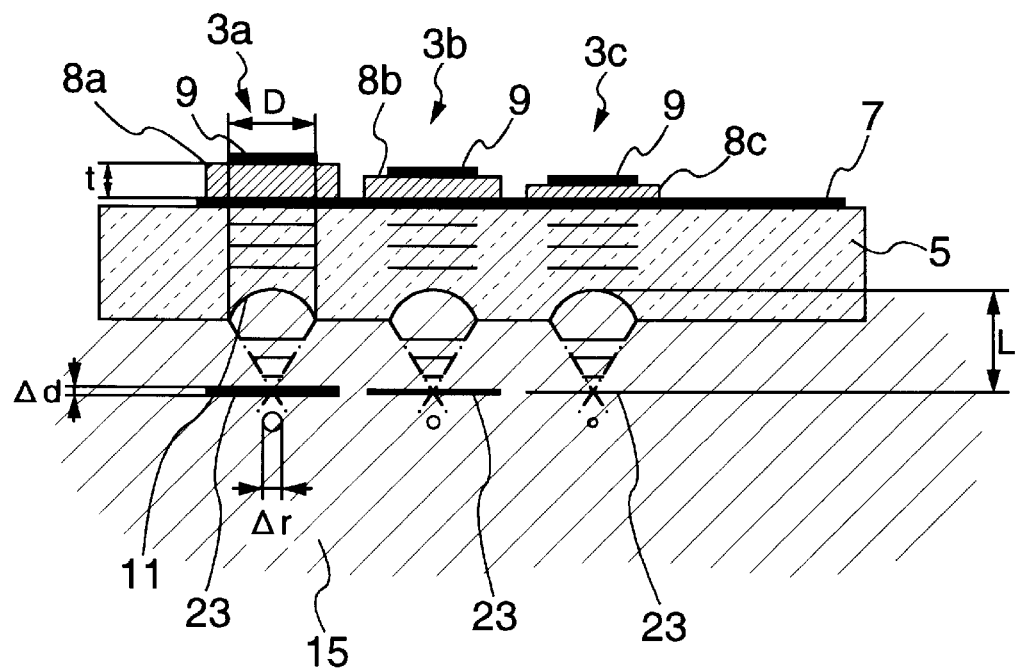

FIG. 10 shows another modified form of the embodiment of FIG. 7, and more specifically is a longitudinal cross-sectional view showing an ultrasonic transducer portion. In this example, piezoelectric elements 8a, 8b and 8c of a plurality of ultrasonic transducers 3a, 3b and 3c have different thicknesses t, respectively, and upper electrodes 9 of the ultrasonic transducers 3a to 3c have the same diameter D, and lens surfaces 11 of the ultrasonic transducers 3a to 3c have the same diameter. Center frequencies of the transducers 3a to 3c are different from one another (If the thickness t of the piezoelectric element is large, the frequency is low, and if the thickness t is small, the frequency is high). The ultrasonic transducers 3a to 3c have the same upper electrodes 9, respectively, and have the same lens condition for converging a produced ultrasonic wave. In this case, the ultrasonic transducers 3a to 3c have the same focal distance L, and images different in the depth Δd of focus and the bearing resolution Δr from one another can be obtained at the same time respectively with respect to three observation positions 23 of the same depth in the patient's body 15. Therefore, without the need for repeating the sticking of the needle as in the conventional construction, the ultrasonic image of different picture qualities can be obtained at the same time. With this construction, a search for an imaging position of the patient's body 15 is made by the ultrasonic transducer 3a of the lower frequency, and an image of a higher resolution is obtained by the ultrasonic transducer 3c of the higher frequency, so that the nature of the tissue can be diagnosed more accurately.

Figure 11:
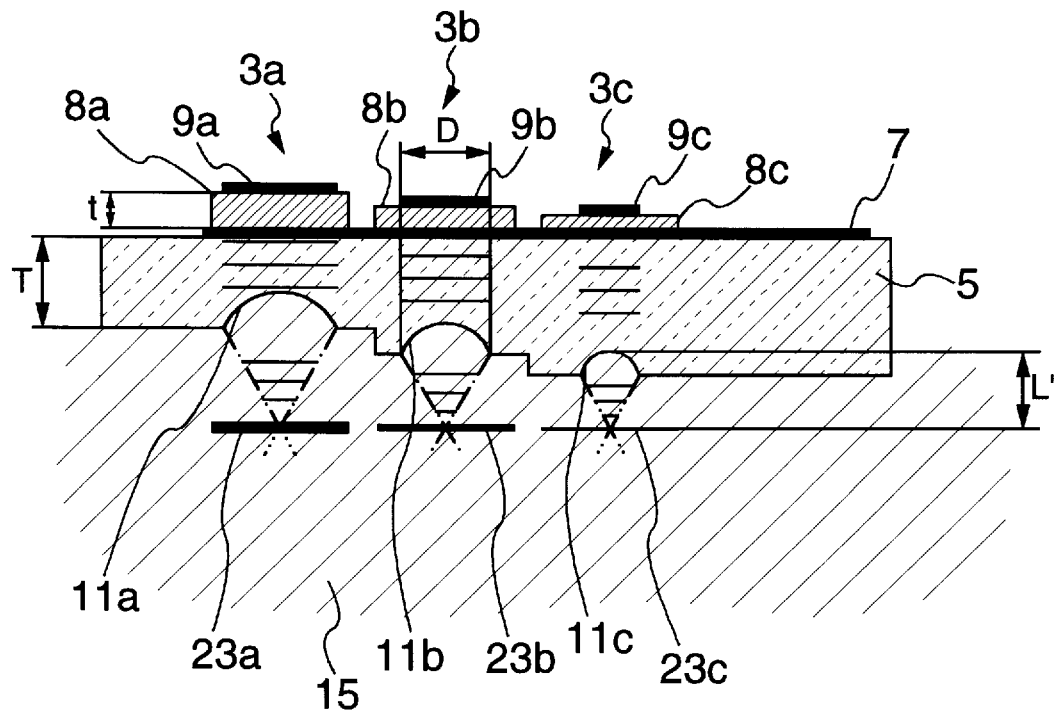

FIG. 11 shows a further modified form of the embodiment of FIG. 7, and more specifically is a longitudinal cross-sectional view showing an ultrasonic transducer portion. In this example, piezoelectric elements 8a, 8b and 8c of a plurality of ultrasonic transducers 3a to 3c have different thicknesses t, respectively, and upper electrodes 9a, 9b and 9c of the ultrasonic transducers 3a to 3c have different diameters D, respectively, and lens surfaces 11a, 11b and 11c of the ultrasonic transducers 3a to 3c have different diameters, respectively. The plurality of ultrasonic transducers 3a, 3b and 3c have different center frequencies, respectively, and have the different upper electrodes 9a, 9b and 9c, respectively, and different lens conditions, respectively, for converging produced ultrasonic waves. A thickness T of an acoustic lens material 5 is varied such that those portions thereof corresponding respectively to the ultrasonic transducers 3a, 3b and 3c have different thicknesses, and with this arrangement, although focal distances of the lens surfaces 11a, 11b and 11c are different from one another, observation positions 23a, 23b and 23c in the patient's body 15 are at the same depth L'. In this case, images different in the depth of focus and the bearing resolution from one another can be obtained at the same time respectively with respect to the three observation positions 23a, 23b and 23c of the same depth L' in the patient's body 15. Therefore, without the need for repeating the sticking of the needle as in the conventional construction, the ultrasonic image of different picture qualities can be obtained at the same time. With this construction, a search for an imaging position of the patient's body 15 is made by the ultrasonic transducer 3a of the lower frequency, and an image of a higher resolution is obtained by the ultrasonic transducer 3c of the higher frequency. Particularly, the degree of absorption of the ultrasonic wave by the tissue of the patient's body 15 is high, and therefore by increasing the thickness T of that portion of the acoustic lens material 5 corresponding to the third ultrasonic transducer 3c, the attenuation of the ultrasonic wave by the living tissue can be reduced. Therefore, the image of a higher resolution can be obtained, so that the nature of the tissue can be diagnosed more accurately.

Figure 12:
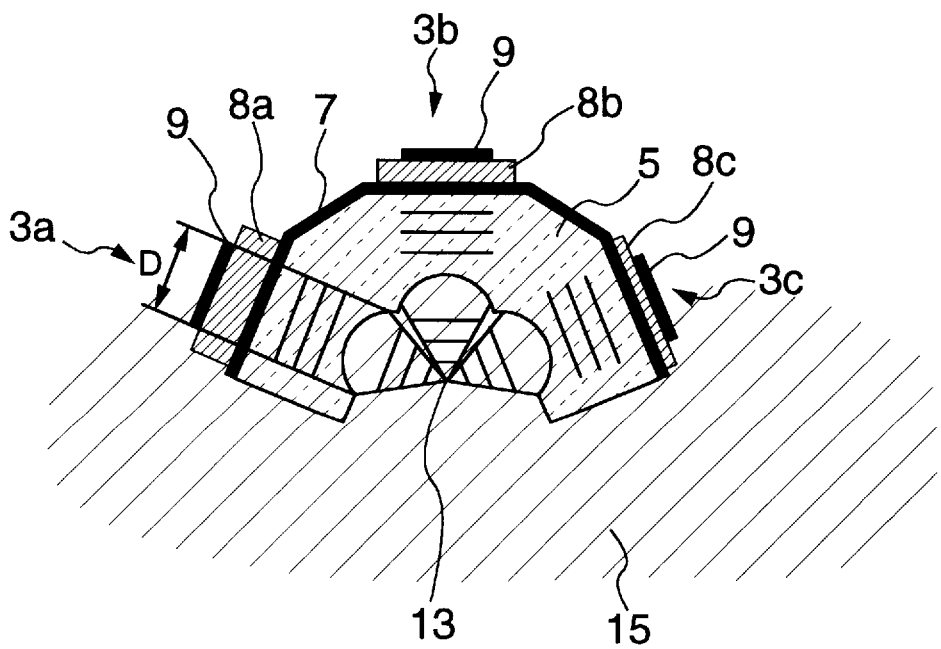
FIG. 12 is a cross-sectional view of a modified form, of the embodiment shown in of FIG. 9, FIG. 10 or FIG. 11.

FIG. 12 is a cross-sectional view of a modifed form of the construction of FIG. 9, FIG. 10 or FIG. 11. In this example, an acoustic lens material 5, serving as a common base, is curved longitudinally, and the arrangement is so made that focuses 13 of ultrasonic waves, produced respectively from ultrasonic transducers 3a, 3b and 3c, can be located at the same position. In the examples of FIGS. 7 to 12, although the three ultrasonic transducers 3a to 3c are provided, the number of the ultrasonic transducers is not limited to three, but a desired number of ultrasonic transducers more than two can be used in the invention.

Figure 13:
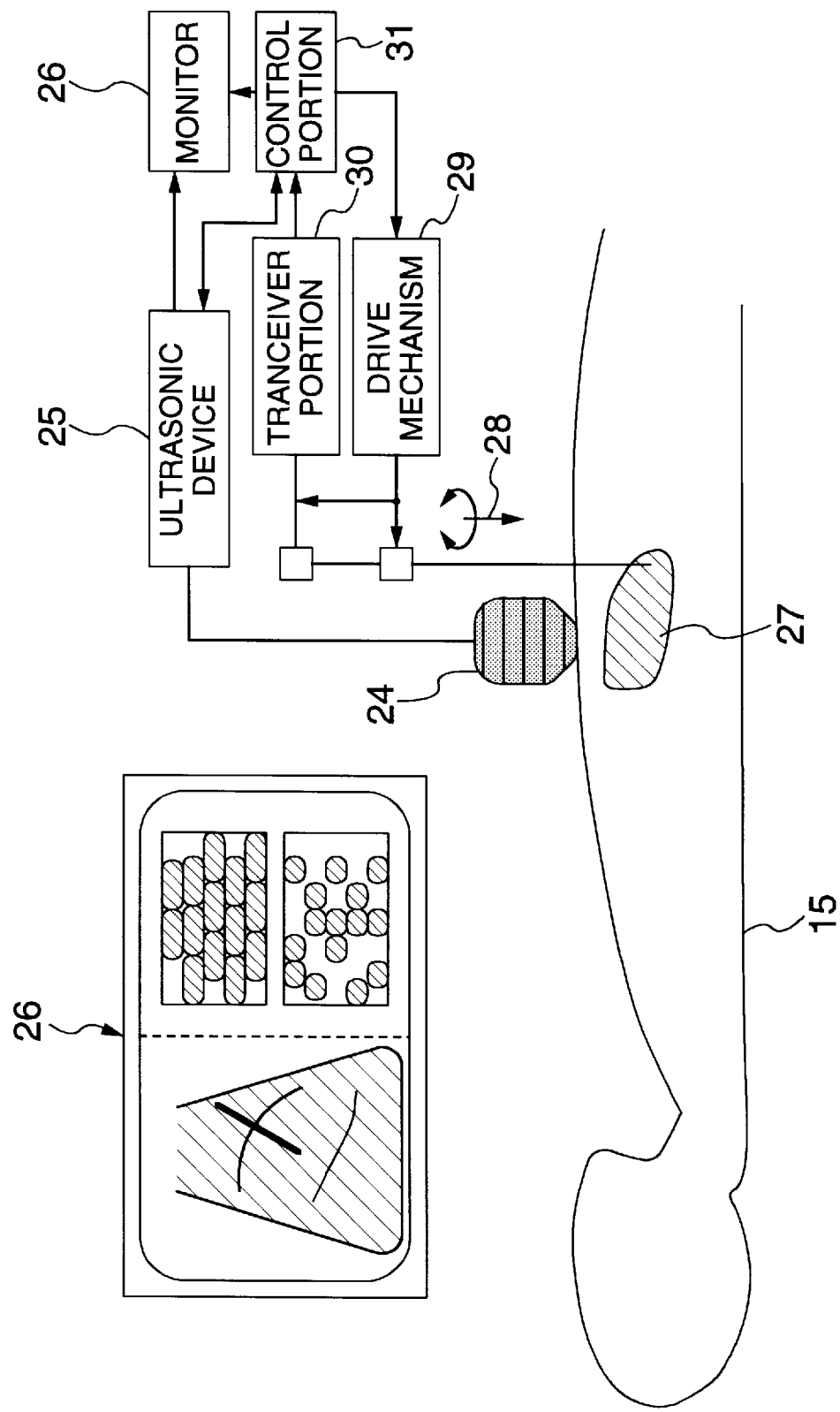
FIG. 13 is a block diagram showing an overall construction of an ultrasonic diagnosis apparatus provided with a needle-like ultrasonic probe of the invention.

FIG. 13 is a block diagram showing an overall construction of an ultrasonic diagnosis apparatus provided with a needle-like ultrasonic probe of the invention. This ultrasonic diagnosis apparatus comprises a probe 24 of the ordinary type for contact with a surface of the patient's body 15, an ultrasonic device 25 for driving the probe 24 and for transmitting and receiving an ultrasonic wave to produce an ultrasonic image, a monitor 26 for receiving an image signal from the ultrasonic device 25 to display the ultrasonic image, the needle-like ultrasonic probe 28 for being stuck into an affected part 27 of the patient's body 15 and for transmitting and receiving an ultrasonic wave, a drive mechanism 29 for sticking the inner needle 2 (see FIG. 1) of the needle-like ultrasonic probe 28 into the affected part 27 and then for rotating and translating the inner needle 2 so as to effect a two-dimensional scanning, a transceiver portion 30 for driving the needle-like ultrasonic probe 28 so as to transmit and receive the ultrasonic wave, and a controller 31 for controlling the portions of the ultrasonic device 25 and the portions of the needle-like ultrasonic probe 28.

In the ultrasonic diagnosis apparatus of the above construction, while observing a tomographic image of the affected part 27 through a screen of the monitor 26 by operating the ordinary probe 24 and the ultrasonic device 25, the inner needle 2 is stuck into a required portion of the affected part 27 by the drive mechanism 29, and a transmitting voltage is applied to the upper electrode 9 of the ultrasonic transducer 3, shown in FIG. 3, through the cable 19 shown in FIG. 1 or FIG. 7, so that the piezoelectric element 8 produces the ultrasonic wave 12 of the required frequency. As a result, this ultrasonic wave 12 is refracted and converged by the lens surface 11 of the acoustic lens material 5 into the focus 13, and a reflected wave from the tissue of the patient's body 15 at this focus position is led to the piezoelectric element 8 through the path of the ultrasonic wave 12', thereby producing a receiving voltage. Then, this receiving voltage is fed to the transceiver portion 30 (shown in FIG. 13) via the cable 19, and the image of the living tissue adjacent to the distal end portion of the needle is displayed on the screen of the monitor 26. Thus, while the ultrasonic waves are transmitted from and received by the needle-like ultrasonic probe 28, the drive mechanism 29 is operated through the controller 31, thereby rotating and translating the inner needle 2 in the imaging area 12 to effect the two-dimensional scanning, as shown in FIG. 2, so that the ultrasonic images of the living tissue of the affect part 27 on a cellular level can be obtained in a real time manner. Namely, as shown in FIG. 13, when the needle-like ultrasonic probe of the present invention is connected to the ultrasonic diagnosis apparatus capable of obtaining and displaying an ordinary tomographic image, the needle-like probe can be accurately guided to the affected part while observing the tomographic image.

Further, as shown in FIG. 13, an image of the living tissue in a non-affected part which can be obtained when the needle-like ultrasonic probe stuck into the tissue does not yet reach the affected part or if the needle-like ultrasonic probe is stuck deeply into the tissue, piercing through the affected part, is displayed on the monitor 26 in the upper part on the right side of the screen thereof together with an image of the living tissue in the affected part which is displayed on the lower part on the right side of the screen of the monitor 26. With this arrangement, in comparison with the image of the living tissue of the affected part and that of the nonaffected part, a difference between the living tissue of the affected part and that of the nonaffected part can be visually found so as to facilitate the diagnosis.

Figure 14A:
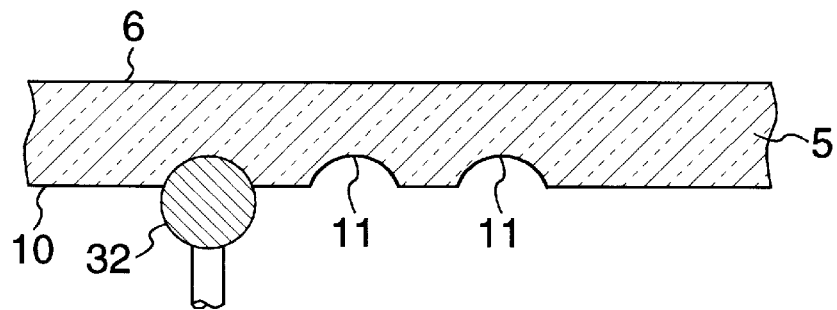
FIGS. 14A to 14D are views showing a method of producing the needle-like ultrasonic probe of the invention.

FIGS. 14A to 14D are views showing a method of producing a needle-like ultrasonic probe of the invention. In this example, the method of producing the needle-like ultrasonic probe having ultrasonic transducers shown in FIG. 10 will be descried. First, as shown in FIG. 14A, a plurality of lens surfaces 11 of a concavely-spherical shape are formed by a mechanical process or a chemical process in one side surface 10 of an acoustic lens material 5 (serving as a common base) which has not yet been cut into a predetermined shape. For example, the acoustic lens material 5 is mechanically ground or polished using a spherical polishing tool 32, or the lens surfaces 11 are chemically formed at a time by photolithography and etching.

Figure 14B:
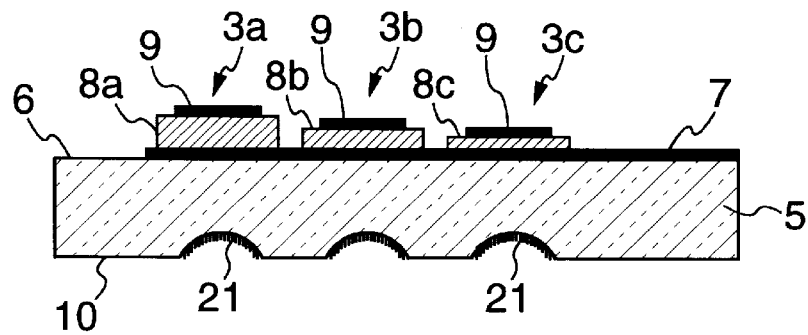

Then, as shown in FIG. 14B, a lower electrode 7, piezoelectric elements 8a, 8b and 8c and upper electrodes 9 are formed by vacuum deposition or sputtering on the other surface 6 of the acoustic lens material 5 in such a manner that the piezoelectric elements 8a to 8c, as well as the upper electrodes 9, are arranged in registry with the three lens surfaces 11, respectively. Concurrently with the above-mentioned process steps, acoustic matching layers 21 are formed respectively on the lens surfaces 11 on the one surface 10 by a thin film-forming process, such as a vapor deposition process or a sputtering process, using a mask having holes of a predetermined size, or by a similar thin film-forming process, photolithography and etching. Then, the acoustic lens material 5 is cut into the predetermined shape, thereby providing the ultrasonic transducers. In this example, the first ultrasonic transducer 3a is composed of the common acoustic lens material 5, the common lower electrode 7, the piezoelectric element 8a and the upper electrode 9, and the second ultrasonic transducer 3b is composed of the common acoustic lens material 5, the common lower electrode 7, the piezoelectric element 8b and the upper electrode 9, and the third ultrasonic transducer 3c is composed of the common acoustic lens material 5, the common lower electrode 7, the piezoelectric element 8c and the upper electrode 9.

Figure 14C:
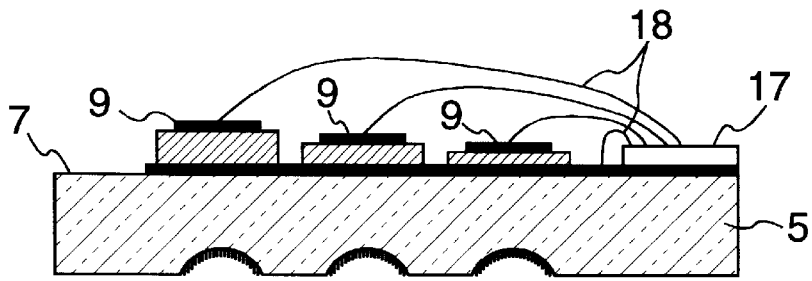

Then, as shown in FIG. 14C, an intermediate base 17 is mounted on the common base, and this intermediate base 17 is connected or wire-bonded to the lower electrode 7 and the upper electrodes 9 by respective signal wires 18.

Figure 14D:
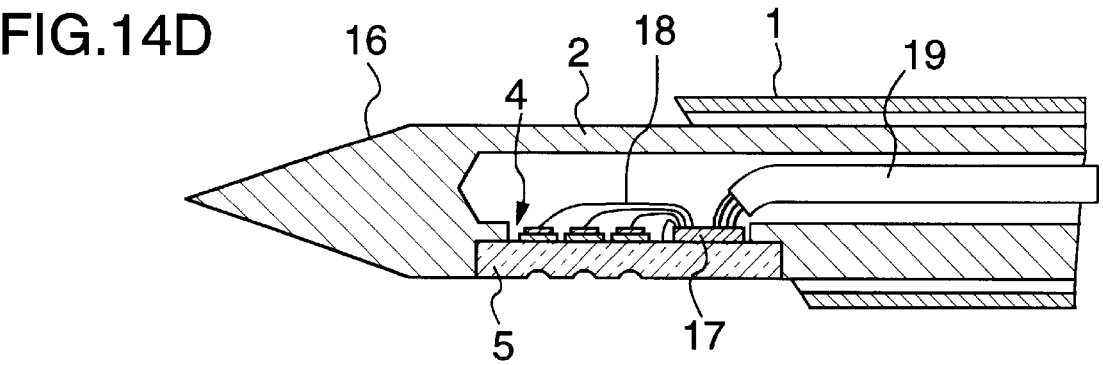

Then, as shown in FIG. 14D, the acoustic lens material 5 (serving as the common base) for the ultrasonic transducers 3a to 3c is fitted and fixed in a mounting groove 4 having a predetermined shape and formed in that portion of an outer peripheral surface of an inner needle 2 which is adjacent to a distal end thereof, and a cable 19 is connected to the intermediate base 17. Finally, the outer peripheral surface of that portion of the inner needle 2, in which the ultrasonic transducers 3a to 3c is provided, is formed into an arcuate cross-sectional shape conforming to the cross-section of the outer peripheral surface of the other portion of the inner needle 2, and the entire outer peripheral surface of the inner needle 2 is finished into a smooth surface. Thus, the needle-like ultrasonic probe of the present invention, which is small in size and diameter, is produced.

Figure 15:
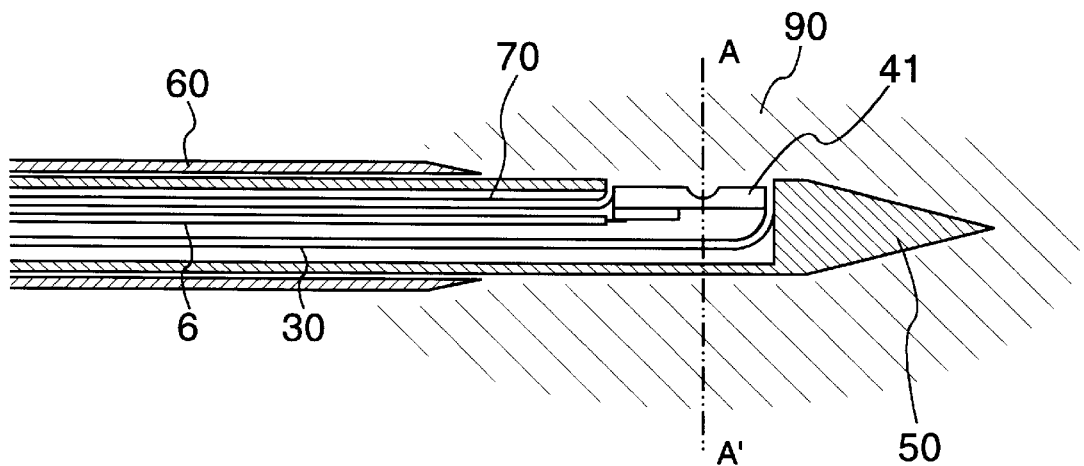
FIG. 15 is a longitudinal cross-sectional view illustrating a third embodiment of a needle-like ultrasonic probe of the invention, taken along an axis thereof.

FIG. 15 is a longitudinal cross-sectional view of a third embodiment of a needle-like ultrasonic probe of the invention, taken along an axis thereof. In this third embodiment, an ultrasonic wave, transmitted from the ultrasonic probe, is converged on the surface of the living tissue, and a reflection signal of a high level is obtained.

Figure 16:
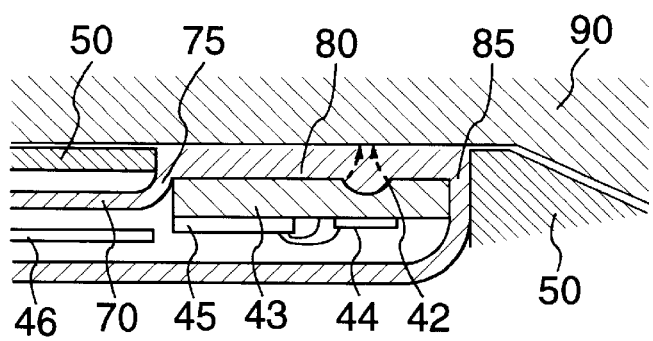
FIG. 16 is an enlarged view illustrating a main portion of the needle-like ultrasonic probe shown FIG. 15.
Figure 17:
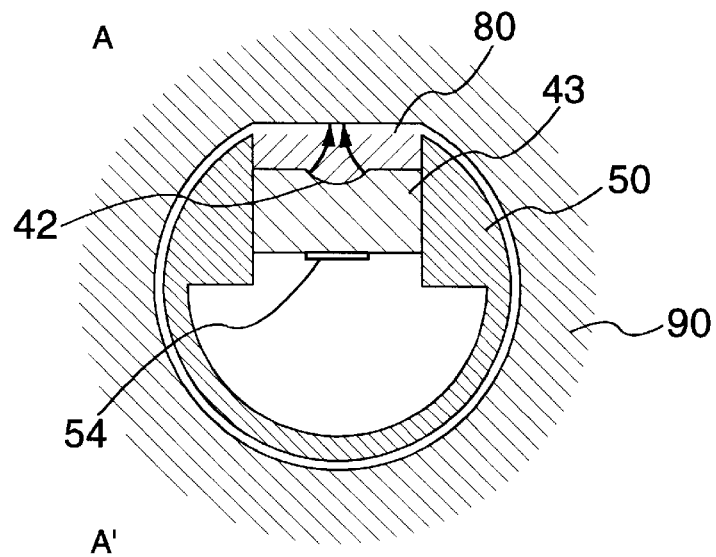
FIG. 17 is a cross-sectional view taken along the line A—A' of FIG. 15.

FIG. 16 is an enlarged view showing a main portion of the needle-like ultrasonic probe of FIG. 15, and FIG. 17 is a cross-sectional view of the needle-like ultrasonic probe taken along the line A—A' of FIG. 15.

Figure 18:
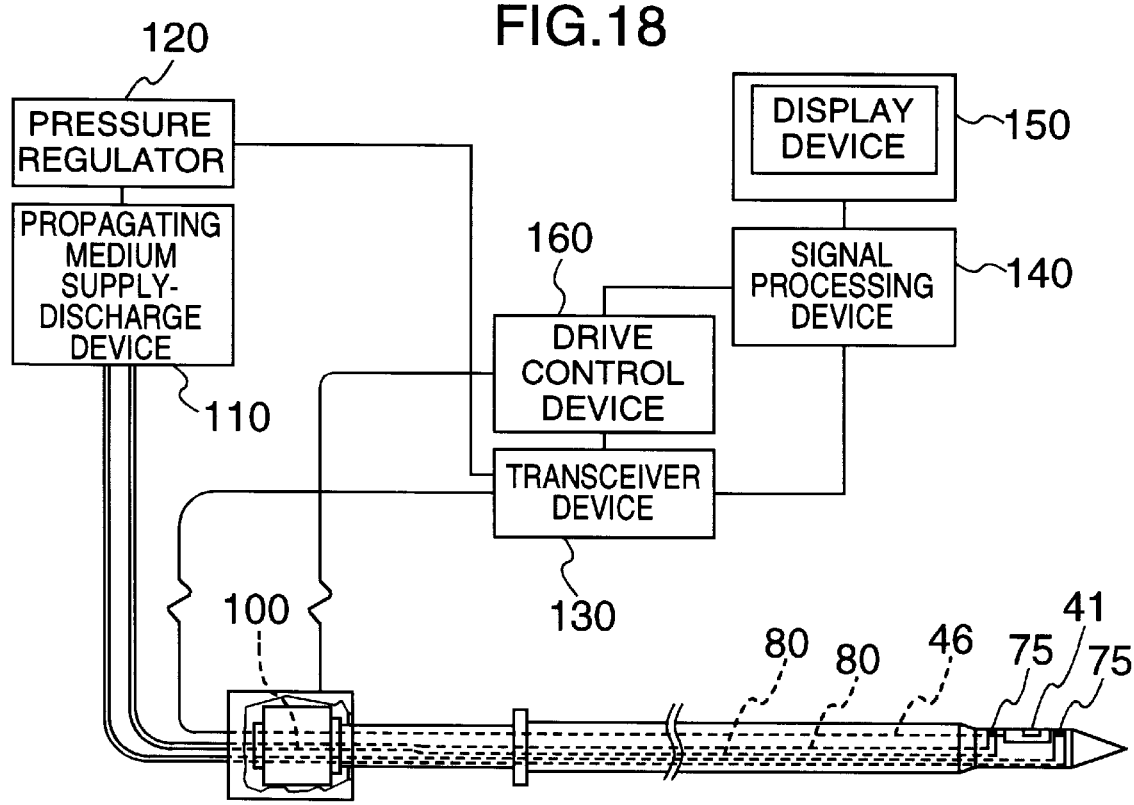
FIG. 18 is a view illustrating the overall construction of the needle-like ultrasonic probe shown in FIG. 15.

FIG. 18 is a view showing the overall construction of the needle-like ultrasonic probe of FIG. 15.

In FIGS. 15 to 18, reference numeral 41 denotes an ultrasonic transducer, reference numeral 42 an acoustic lens, reference numeral 43 a base plate, reference numeral 44 an oscillator, reference numeral 45 a signal wire-mounting board, reference numeral 46 a signal wire, reference numeral 50 an inner needle, reference numeral 60 an outer needle, reference numeral 70 a sound-propagating medium supply-discharge conduit, reference numeral 75 an opening or port of the sound-propagating medium supply-discharge conduit, reference numeral 80 a liquid sound-propagating medium, reference numeral 90 a living tissue, reference numeral 100 a drive portion, reference numeral 110 a device for supplying and discharging the sound-propagating medium 80, reference numeral 120 a pressure regulator, reference numeral 130 a transceiver device, reference numeral 140 a signal processing device, reference numeral 150 a display device, and reference numeral 160 a drive control device.

The ultrasonic transducer 41 comprises the base plate 43 having the lens formed therein, and the thin film oscillator 44 formed on the base plate 43.

An ultrasonic wave, transmitted from the oscillator 44, propagates through the base plate 43, and then is converged by the acoustic lens 43, and enters the living tissue 90. The ultrasonic wave, reflected from the living tissue 90, goes back along the above-mentioned path, and is received by the oscillator 44.

The base plate 43 is made, for example, of sapphire, and the oscillator 44 is made, for example, of zinc oxide (ZnO).

The ultrasonic transducer 41 is mounted in the inner needle 50 of the needle-like ultrasonic probe, and the scanning of the living tissue 90 therearound by the ultrasonic transducer 41 is effected by moving the inner needle 50.

Therefore, the drive portion 100 for driving the inner needle 50 is provided at the proximal end of the inner needle 50, and the drive portion 100 is controlled by the drive control device 160.

The outer needle 60 protects the ultrasonic transducer 41, and also prevents the inner needle 50 from shaking during the scanning operation. The outer needle 60 receives the inner needle 50 therein except the distal end thereof when the prove is stuck into the living tissue, and when the measurement is to be effected, the outer needle 60 allows the ultrasonic transducer 41 to be exposed, as shown in FIG. 15.

Here, the inner needle 50 and the outer needle 60 are both made of stainless steel.

Preferably, the diameter of the inner needle 50 is about 1.6 mm to about 1 mm, and the diameter of the acoustic lens is about 200 $\mu$m, and the frequency of the ultrasonic wave is about 200 MHz.

The supply of a transmitting voltage to the oscillator 44 via the signal wire 46, as well as the detection of a receiving voltage, is effected by the transceiver device 130.

The signal processing device 140 feeds instructions to the drive control device 160 so as to effect the scanning movement of the needle-like ultrasonic probe by the drive portion 100, the control of the transmitting and receiving waves, the formation of an image by a detection signal, and the display of the image on the display device 150.

In the needle-like ultrasonic probe of this embodiment, the inner needle 50 is moved, for scanning, spirally so as to obtain a C-mode image.

The liquid sound-propagating medium 80, supplied through the sound-propagating medium supply-discharge conduit 70, is interposed between the acoustic lens 42 and the living tissue 90.

The device 110 for supplying and discharging the liquid sound-propagating medium 80, which device can adjust a hydrostatic pressure, is connected to proximal or rear ends of the sound-propagating medium supply-discharge conduits 70.

By changing this hydrostatic pressure, the position of the interface between the living tissue 90 and the liquid sound-propagating medium 80 is finely adjusted to be brought into agreement with the position of the focus of the acoustic lens 42.

The distance between the acoustic lens 42 and the living tissue 90 can be monitored from the time difference between the time when the oscillator 44 transmits an ultrasonic wave and the time when this ultrasonic wave, reflected at the interface between the living tissue 90 and the liquid sound-propagating medium 80, is received by the oscillator 44.

Therefore, this time difference is detected by the transceiver device 130 as shown in FIG. 18, and in accordance with this detected time difference, the pressure is controlled, thereby effecting the positioning of the above interface.

In this embodiment, there are provided the two sound-propagating supply-discharge conduits 70, and one of them is used for supplying the sound-propagating medium while the other is used for discharging the sound-propagating medium.

With this construction, when the blood oozes from the living tissue 90 to be present between the acoustic lens 42 and the living tissue 90, thereby inhibiting observation by the ultrasonic wave, the liquid sound-propagating medium 80 is caused to flow to clean this living tissue 90.

An acoustic impedance of the cells in an internal organ (the living tissue 90), is usually 1.35 to $1.8 \times 10^6$ (kg/m$^2$s), and an acoustic impedance of water is about $1.5 \times 10^6$ (kg/m$^2$s). Therefore, when a liquid, having a high acoustic impedance, such as glycerin, is used as the liquid sound-propagating medium 80, the intensity of the signal increases.

However, since the liquid sound-propagating medium 80 remains in the living tissue even after the examination, a harmless liquid such as physiologic saline is used as the liquid sound-propagating medium 80.

When physiologic saline is used as the liquid sound-propagating medium 80, the reflectance at the interface between the living tissue and the sound-propagating medium is at least 10 times as large as the reflectance caused by the distribution of the acoustic impedance in the living tissue.

If the blood, oozing from an internal organ (e.g. the liver) when measuring the tissue of the internal organ, serves as a sound-propagating medium, it is not necessary to supply the sound-propagating medium from the exterior.

Figure 19:
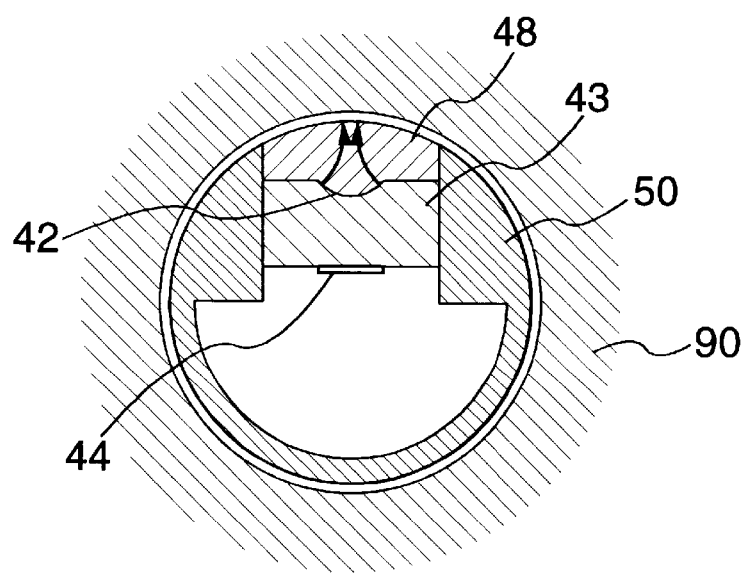
FIG. 19 is an enlarged view illustrating a main portion of a needle-like ultrasonic probe according to a fourth embodiment of the invention.

FIG. 19 is an enlarged view showing a main portion of a fourth embodiment of a needle-like ultrasonic probe of the invention.

In FIG. 19, reference numeral 42 denotes an acoustic lens, reference numeral 43 a base plate, reference numeral 44 an oscillator, reference numeral 48 a solid sound-propagating medium, reference numeral 50 an inner needle, and reference numeral 90 a body's tissue.

The needle-like ultrasonic probe of this embodiment differs from the needle-like ultrasonic probe of the third embodiment in that the solid sound-propagating medium 48, made for example of polyethylene, is used.

With the construction of this embodiment, the cross-section of the inner needle 50 can be made completely circular, and when this inner needle 50 is used, during movement for scanning, the needle 50 will not damage the tissue therearound.

If the scanning movement of the inner needle 50 can be effected smoothly by the body fluid oozing from the tissue therearound, it is not necessary to supply a liquid sound-propagating medium 80, and supply-discharge conduits 70 are not necessary.

Of course, if a liquid sound-propagating medium is necessary for effecting the smooth scanning movement of the inner needle 50 and/or for washing out the blood, the liquid sound-propagating medium 80 can be supplied between the acoustic lens 42 and the body's tissue 90 as in the third embodiment.

As described above, it is preferred that an acoustic impedance of the solid sound-propagating medium 48 should be different from that of the living tissue 90, and this acoustic impedance is preferably not less than $2.0 \times 10^6$ (kg/m$^2$s).

If the sound-propagating medium is the solid sound-propagating medium 48, it will not remain in the body after the examination, and a range of choice for materials of the solid sound-propagating medium is wider in comparison with the liquid sound-propagating medium.

However, for example, if the lens material is sapphire, and the acoustic impedance of the sound-propagating medium is too close to the acoustic impedance (about $44 \times 10^6$(kg/m$^2$s)) of sapphire, then an ultrasonic wave is less liable to be refracted by the acoustic lens 42.

Polyethylene does not attenuate an ultrasonic wave too much, and is suitable for use as a material of the sound-propagating medium.

In the above-mentioned third and fourth embodiments, for simplicity, only one ultrasonic transducer is used.

A fifth embodiment of the invention is directed to a method of determining the arrangement of a plurality of ultrasonic transducers on a needle-like ultrasonic probe.

Figure 20:
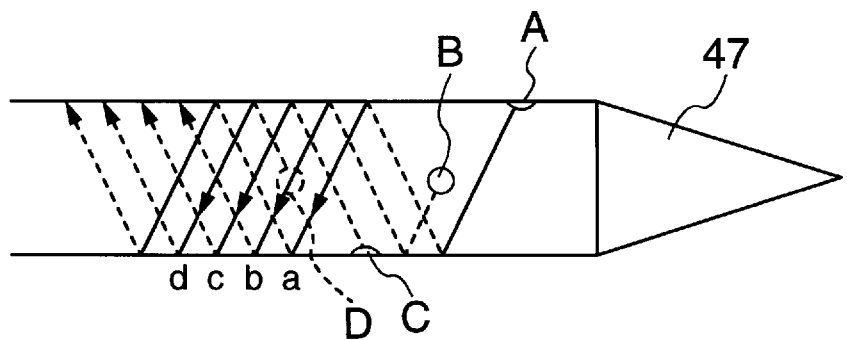
FIG. 20 is a view illustrating the needle-like ultrasonic probe of a fifth embodiment, in which one example of arrangement of a plurality of ultrasonic transducers is shown.
Figure 21:
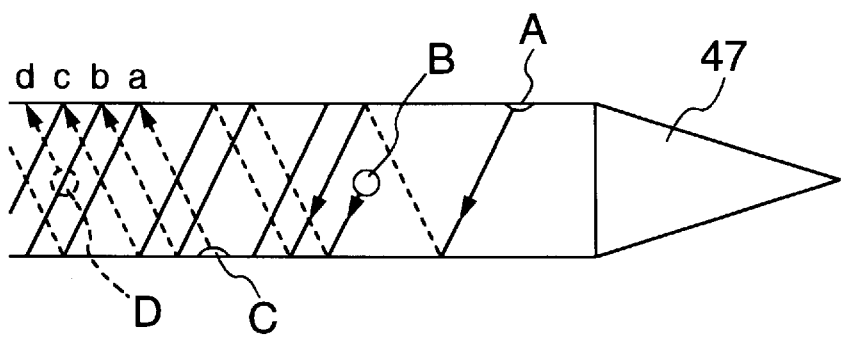
FIG. 21 is a view similar to FIG. 20, but illustrating a modified form of arrangement of a plurality of ultrasonic transducers.
Figure 22:
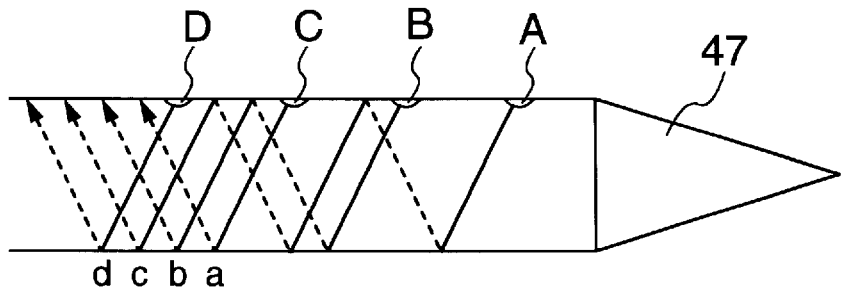
FIG. 22 is a view similar to FIG. 20, but illustrating another modified form of arrangement of a plurality of ultrasonic transducers.

FIGS. 20, 21 and 22 respectively show examples of methods of arranging a plurality of ultrasonic transducers on a needle-like ultrasonic probe in the fifth embodiment.

Figure 23:
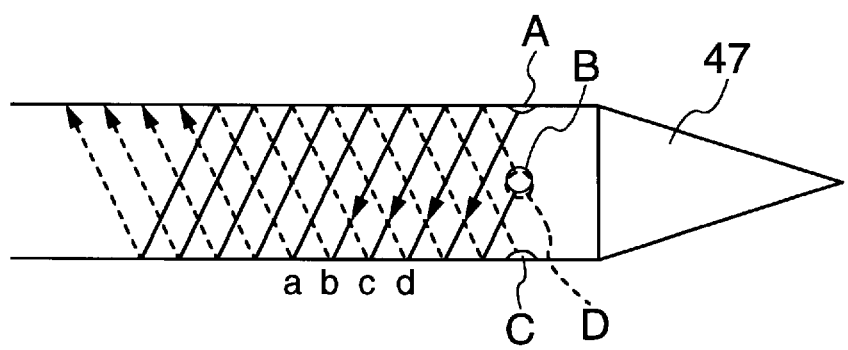
FIG. 23 is a view illustrating the simplest method of arranging a plurality of ultrasonic transducers on a needle-like ultrasonic probe.

FIG. 23 shows the simplest method of arranging a plurality of ultrasonic transducers on a needle-like ultrasonic transducer.

In FIGS. 20 to 23, for illustration purposes, the positions of the ultrasonic transducers are indicated by circles, respectively, and scanning lines during the scanning are shown.

Each of FIGS. 20 to 23 shows that portion of the needle-like ultrasonic probe 47 corresponding to the inner needle 50 shown in FIG. 15.

Figure 24:
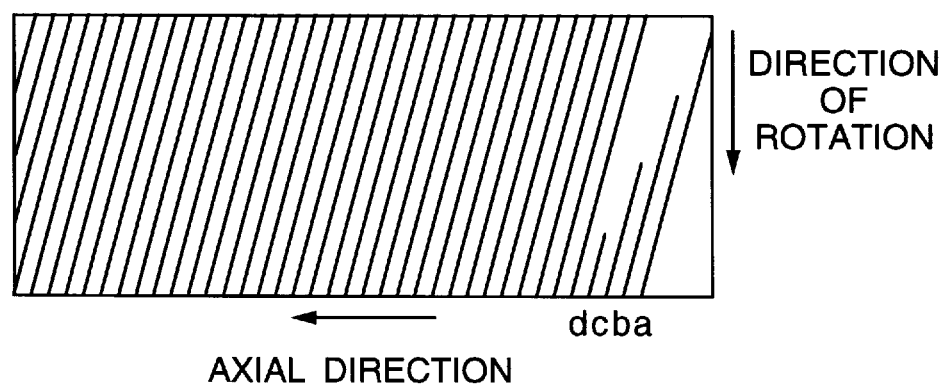
FIG. 24 is a view schematically showing scanning lines of an image obtained when moving, for scanning, the needle-like ultrasonic probe in the case of the arrangement of FIG. 20.
Figure 25:
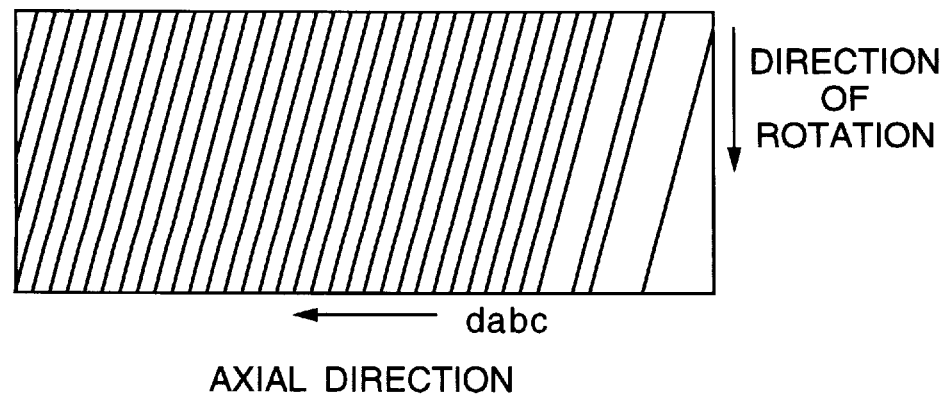
FIG. 25 is a view schematically showing scanning lines of an image obtained when moving, for scanning, the needle-like ultrasonic probe in the case of the arrangement of FIG. 22.
Figure 26:
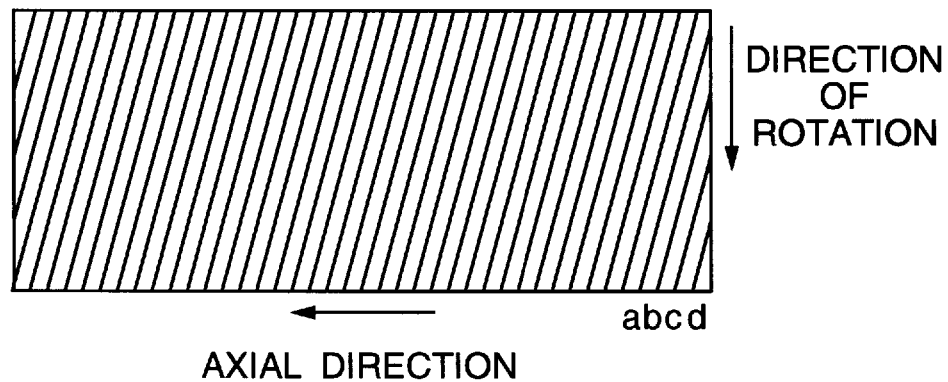
FIG. 26 is a view schematically showing scanning lines of an image obtained when moving, for scanning, the needle-like ultrasonic probe in the case of the arrangement of FIG. 23.
Figure 27:
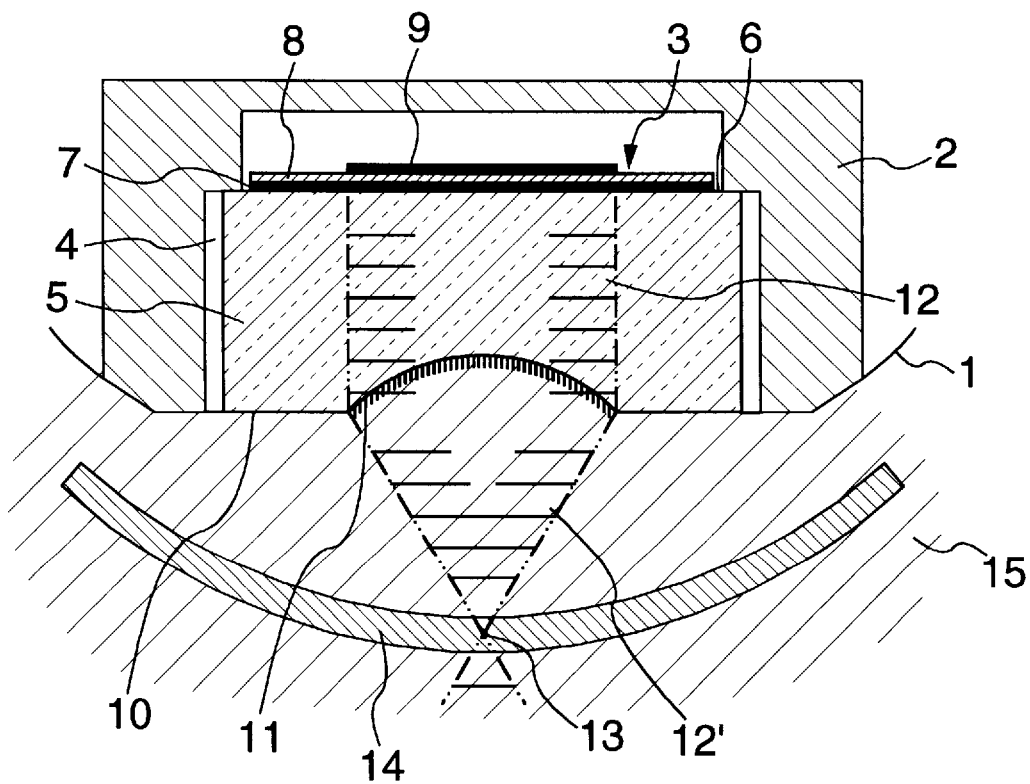
FIG. 27 is an enlarged, cross-sectional view illustrating a main portion of an ultrasonic transducer in a conventional needle-like ultrasonic probe.

FIGS. 24, 25 and 26 are views schematically showing the scanning lines of images obtained when the needle-like ultrasonic probe 47 is moved spirally for scanning.

In the needle-like ultrasonic probe of the fifth embodiment, estimating that the number of the ultrasonic transducers mounted thereon is represented by m, and that the distance of movement in the axial direction per rotation in the spiral scanning is represented by p. In this case, if the position of the s-th ultrasonic transducer in the rotational direction is represented by θs degrees, using the position of the 1-st ultrasonic transducer as a reference, the position thereof in the axial direction is expressed by the following formula (1):

$$p \, [(\theta s/360) + (s-1)\{n + (t/m)\}] \quad (1)$$

where n represents an integer, and t represents 1 or a natural number which is less than m, and is prime to m.

In each of the examples shown respectively in FIGS. 20 to 23, the number (m) of the ultrasonic transducers is 4, and the 1st, 2nd, 3rd and 4th ultrasonic transducers are indicated by A, B, C and D, respectively, and the scanning lines of these ultrasonic transducers being indicated by a, b, c and d, respectively.

When mounting the plurality of ultrasonic transducers, the simplest method of arranging these ultrasonic transducers is that shown in FIG. 23, and in this method the four ultrasonic transducers are spaced an equal distance from one another in the direction of rotation of the inner needle, and also are disposed at the same position (that is, in a common plane perpendicular to the axis of the inner needle) in the axial direction.

In the arrangement method shown in FIG. 23, n=−1 and t=3 are provided in the above formula (1).

FIG. 26 show the scanning lines obtained when the ultrasonic transducers are arranged as shown in FIG. 23.

Naturally, for obtaining the same scanning line density, the time required with the provision of four ultrasonic transducers is ¼ of the time required with the provision of one ultrasonic transducer.

However, as will be appreciated from FIG. 17, it is difficult to arrange the plurality of ultrasonic transducers in the narrow inner needle 50 in a manner shown in FIG. 23.

Therefore, the ultrasonic transducers are arranged, for example, in a manner shown in FIG. 20.

In the arrangement method shown in FIG. 20, the position θ2 of the 2nd ultrasonic transducer in the rotational direction is 90°, and the position θ3 of the 3rd ultrasonic transducer in the rotational direction is 180°, and the position θ4 of the 4th ultrasonic transducer in the rotational direction 270°.

In the arrangement method shown in FIG. 20, n=0 and t=1 are provided in the above formula (1). In other words, the ultrasonic transducers are spaced by an equal distance from one another in the direction of rotation of the inner needle 50, and also are spaced in the axial direction from one another by a distance twice the spacing of the scanning lines of the image to be obtained.

FIG. 24 shows the scanning lines obtained when the ultrasonic transducers are arranged in a manner shown in FIG. 20. These scanning lines are different from those of FIG. 26 only in a starting portion, and the scanning line density in FIG. 24 is the same as that in FIG. 26.

However, since the ultrasonic transducers are spaced from one another in the axial direction, the mounting of these ultrasonic transducers can be effected more easily.

Similarly, if n=0 and t=0 are provided in the above formula (1), the arrangement method shown in FIG. 21 is obtained.

If the value of t is 2 which is a factor of 4, the scanning lines overlap each other.

As in the arrangement method shown in FIG. 21, there is a requirement for the value of t, and t should be 1 or a natural number which is less than m, and is prime to m.

Here, if the number of the ultrasonic transducers is 4, the value of t is 1 or 3.

In the arrangement method shown in FIG. 22, the positions of all of the ultrasonic transducers in the rotational direction are 0°.

In the arrangement method shown in FIG. 22, n=0 and t=3 are provided in the above formula (1), and FIG. 25 shows the scanning lines obtained when the ultrasonic transducers are arranged in a manner shown in FIG. 22.

With the arrangement method of FIG. 22, also, the density of mounting of the ultrasonic transducers can be reduced without changing the scanning line density from that of FIG. 26.

The present invention should not be limited to the above embodiments, and various modifications can be made without departing from the scope of the invention.

In the needle-like ultrasonic probe of the invention, the inner needle is made of a rigid material, and is in the form of a bar of a circular cross-section having a small diameter, and the outer peripheral surface of that portion of the inner needle, which is disposed adjacent to the conical distal end thereof, and has the ultrasonic transducer provided therein, is formed into an arcuate cross-sectional shape conforming to the cross-section of the outer peripheral surface of the other portion of the inner needle, and the entire outer peripheral surface of the inner needle is finished into a smooth surface. With this construction, when the inner needle is stuck directly into the living tissue, the inner needle less affects the living tissue. For example, even when the inner needle is rotated so as to effect the ultrasonic scanning, the living tissue of the patient's body will not be damaged. The above arcuate surface is extended to the position near to the focus of the ultrasonic transducer, and therefore the degree of absorption of the ultrasonic wave by the patient's body is low, and this prevents the sound field from being disturbed. Therefore, the ultrasonic image of a high quality can be obtained.

In the needle-like ultrasonic probe in which the plurality of ultrasonic transducers are mounted on the common base composed of the acoustic lens material, the range of the image formation per rotation of the inner needle becomes larger by several times, and the time required for effecting the two-dimensional scanning over the entire imaging area can be reduced. Therefore, the ultrasonic images of the body's tissue of the patient's body can be obtained in a short period of time, and also when the inner needle is stuck once, the ultrasonic images, having different measurement conditions, can be obtained at the same time. This reduces the burden on the patient.

In the production method of the invention, the above needle-like ultrasonic probe is formed by the thin film process, the photolithography process, the etching process or the like, and therefore even the needle-like ultrasonic probe, having the plurality of ultrasonic transducers mounted thereon, can be produced into the small-size and small-diameter design.

In the present invention, the needle-like ultrasonic probe includes at least one ultrasonic transducer for transmitting and receiving an ultrasonic wave in a direction perpendicular to the axis thereof, and this probe is stuck into the living tissue so as to measure the living tissue therearound. The position of the focus, into which the ultrasonic wave, transmitted from and received by the ultrasonic transducer, is converged in the liquid sound-propagating medium by the acoustic lens, is caused to coincide with the position of the interface between the living tissue and the sound-propagating medium in the range of the depth of the focus. Therefore, the acoustic impedance difference is larger, so that the intensity of the reflectance signal can be increased by more than 10 times.

Therefore, the gradation of the obtained images can be increased, and a diagnosis by the use of the needle-like ultrasonic probe can be made easily.

In the present invention, the plurality of ultrasonic transducers can be mounted at a reduced density on the needle-like ultrasonic probe, and the scanning lines of the ultrasonic transducers do not overlap with each other, and are arranged at equal intervals so that the optimum configuration can be obtained.

Therefore, the time required for collecting the necessary images can be reduced, and this reduces the burden on the patient.

What is claimed is:

1. A needle-like ultrasonic probe comprising:

a hollow, tubular outer needle which is made of a rigid material, and has a small diameter;

an inner needle which is made of a rigid material, and is in the form of a bar of a circular cross-section having a small diameter, said inner needle being received in said outer needle for rotation about an axis thereof and for translation along the axis thereof, and said inner needle having a distal end of a conical shape; and at least one ultrasonic transducer for transmitting and receiving an ultrasonic wave, said ultrasonic transducer being mounted at that portion of an outer peripheral surface of said inner needle which is located adjacent to said distal end thereof;

wherein said inner needle and said outer needle are stuck into a patient's body, and an ultrasonic wave is transmitted from and received by said ultrasonic transducer, and said inner needle is rotated and translated to effect two-dimensional scanning so as to obtain an ultrasonic image of a tissue of the patient's body; and wherein the outer peripheral surface of that portion of said inner needle, which is located adjacent to said distal end thereof, and which has said ultrasonic transducer provided therein, is formed into an arcuate cross-sectional shape conforming to the cross-section of the outer peripheral surface of the other portion of said inner needle, and the entire outer peripheral surface of said inner needle is finished into a smooth surface.

2. A needle-like ultrasonic probe according to claim 1, in which a plurality of said ultrasonic transducers are mounted on a common base which is mounted at that portion of the outer peripheral surface of said inner needle which is located adjacent to said distal end thereof, and is composed of an acoustic lens material, and said acoustic lens material causes the ultrasonic wave to converge into a position which is located at a point of a living tissue slightly spaced from an interface between said acoustic lens material and the living tissue.

3. A needle-like ultrasonic probe according to claim 2, in which said plurality of ultrasonic transducers have the same center frequency, and have the same upper electrodes, respectively, and have the same lens condition for converging the produced ultrasonic wave.

4. A needle-like ultrasonic probe according to claim 2, in which said plurality of ultrasonic transducers have the same or different center frequencies, and have the same or different upper electrodes, respectively, and have the same or different lens conditions for converging the produced ultrasonic wave.

5. A needle-like ultrasonic probe according to claim 2, in which said plurality of ultrasonic transducers have different center frequencies, respectively, and have different upper electrodes, respectively, and have different lens conditions for converging the produced ultrasonic wave.

6. A needle-like ultrasonic probe according to any one of claims 2 to 5, in which said plurality of ultrasonic transducers are arranged on a curved surface such that focuses of the ultrasonic waves, produced respectively from said plurality of ultrasonic transducers, are located at the same position.

7. A method of producing a needle-like ultrasonic probe comprising the steps of:

a plurality of lens surfaces are formed in one surface of an acoustic lens material by a mechanical process or a chemical process;

subsequently forming a lower electrode, piezoelectric elements and upper electrodes on the other surface of said acoustic lens material by vacuum deposition or sputtering in such a manner that said piezoelectric elements, as well as said upper electrodes, are located in registry with said plurality of lens surfaces, respectively;

subsequently cutting said acoustic lens material into a predetermined shape, thereby providing ultrasonic transducers;

subsequently mounting an intermediate base on said acoustic lens material, and connecting said intermediate base to said lower electrode and said upper electrodes by respective signal wires;

subsequently fitting and fixing said acoustic lens material in a mounting groove formed in that portion of an outer peripheral surface of an inner needle which is adjacent to a distal end thereof;

subsequently connecting a cable to said intermediate base; and subsequently forming the outer peripheral surface of that portion of said inner needle, in which said acoustic lens material is fitted, into an arcuate cross-sectional shape conforming to the cross-section of the outer peripheral surface of the other portion of said inner needle, and finishing the entire outer peripheral surface of said inner needle into a smooth surface.

8. A needle-like ultrasonic probe for being stuck into a living body so as to measure an ambient body's tissue by an ultrasonic wave, said probe comprising:

an acoustic lens for converging the ultrasonic wave;

at least one ultrasonic transducer for transmitting and receiving the ultrasonic wave in a direction substantially perpendicular to an axis of said probe;

means for measuring a time difference between a time of transmitting the ultrasonic wave from said at least one ultrasonic transducer and a time of receiving the ultrasonic wave through said at least one ultrasonic transducer;

supply-discharge conduit means for supplying and discharging a liquid sound-propagating medium, said supply-discharge conduit means including at least a first conduit for supplying said liquid sound-propagating medium and a second conduit for discharging said liquid sound-propagating medium; and means provided at one end of said supply-discharge conduit means, remote from said acoustic lens, for supplying and discharging said liquid sound-propagating medium under a pressure which is adjusted in accordance with said time difference;

wherein said liquid sound-propagating medium is supplied between said acoustic lens and said tissue to be measured through said supply-discharge conduit means; and wherein the position of a focus into which the ultrasonic wave transmitted from and received by said at least one ultrasonic transducer, is converged in said liquid sound-propagating medium by said acoustic lens, is caused to coincide with the position of an interface between said tissue to be measured and said sound-propagating medium in a range of a depth of the focus of said acoustic lens at least during the measurement.

9. A needle-like ultrasonic probe comprising:

a plurality of ultrasonic transducers each for transmitting and receiving an ultrasonic wave in a direction substantially perpendicular to an axis of a needle of said probe, said plurality of ultrasonic transducers being spaced at equal intervals in a direction of rotation of said needle of said probe, and at equal intervals in an axial direction of said needle;

wherein said probe is inserted into a living body, and is scanningly moved spirally, thereby obtaining images of a living tissue therearound; and wherein said ultrasonic transducers are arranged on a spiral line around the axis of said probe, and a position of respective ones of said ultrasonic transducers in the axial direction of said probe as measured from a foremost first ultrasonic transducer is expressed by the following formula:

$$p[(\theta s/360)+(S-1)\{n+(t/m)\}]$$

where m is the number of ultrasonic transducers, p is the distance of axial movement per rotation in the spiral scanning, θs degrees is the position of S-th ultrasonic transducer in the rotational direction, n is an integer, and t is 1 or natural number which is less than m and is prime to m.

10. A needle-like ultrasonic probe according to claim 9, wherein said ultrasonic transducers are located on a line along said axis of said probe.

11. A needle-like ultrasonic probe according to claim 9, wherein each of said ultrasonic transducers are located on a circle having a center located on said axis of said probe.

12. An ultrasonic diagnosis apparatus comprising:

a first probe for contact with a surface of a patient's body;

means for driving said first probe so as to produce an ultrasonic tomographic image of a living tissue of the patient's body;

a needle-like ultrasonic probe for transmitting and receiving an ultrasonic wave; and means for sticking an inner needle of said needle-like ultrasonic probe and then for rotating and translating said inner needle so as to effect a two-dimensional scanning;

wherein said inner needle is stuck into a required portion of an affected part in the living tissue by said means for sticking, said means for driving drives said first probe so as to produce a tomographic image of the affected part which is observed through a monitor, and an image of the living tissue adjacent to a distal end portion of said inner needle is displayed on said monitor.

13. An apparatus as set forth in claim 12, wherein said monitor has a screen on which an image of a living tissue of a non-affected part obtained by said needle-like ultrasonic probe is also displayed together with the image of the living tissue of said affected part.

* * * * *